United States Patent
Xing et al.

(10) Patent No.: US 11,021,419 B2
(45) Date of Patent: *Jun. 1, 2021

(54) DEHYDROGENATION CATALYSTS AND METHODS FOR PREPARING AND USING THEM

(71) Applicant: Clariant International Limited, Pratteln (CH)

(72) Inventors: Rong Xing, Louisville, KY (US); Vladimir Fridman, Louisville, KY (US)

(73) Assignee: Clariant International Ltd., Muttenz (CH)

( * ) Notice: Subject to any disclaimer, the term of this patent is extended or adjusted under 35 U.S.C. 154(b) by 14 days.

This patent is subject to a terminal disclaimer.

(21) Appl. No.: 16/246,682

(22) Filed: Jan. 14, 2019

(65) Prior Publication Data
US 2020/0223767 A1   Jul. 16, 2020

(51) Int. Cl.
| | |
|---|---|
| *C07C 5/32* | (2006.01) |
| *B01J 23/63* | (2006.01) |
| *B01J 23/10* | (2006.01) |
| *B01J 23/656* | (2006.01) |
| *B01J 23/89* | (2006.01) |

(Continued)

(52) U.S. Cl.
CPC .............. *C07C 5/322* (2013.01); *B01J 21/04* (2013.01); *B01J 21/12* (2013.01); *B01J 23/002* (2013.01); *B01J 23/10* (2013.01); *B01J 23/63* (2013.01); *B01J 23/6562* (2013.01); *B01J 23/896* (2013.01); *B01J 37/0236* (2013.01); *B01J 37/036* (2013.01); *B01J 37/08* (2013.01)

(58) Field of Classification Search
CPC ......... C07C 5/322; B01J 37/036; B01J 37/08; B01J 23/63; B01J 23/002; B01J 23/896; B01J 37/0236; B01J 23/6562; B01J 23/10; B01J 21/12; B01J 21/04
See application file for complete search history.

(56) References Cited

U.S. PATENT DOCUMENTS 10,307,737 B2   6/2019   Kim

FOREIGN PATENT DOCUMENTS

| CN | 105582929 |   | 5/2016 | |
|---|---|---|---|---|
| CN | 105582929 B | * | 6/2018 | ............. B01J 23/63 |
| EP | 1074299 |   | 2/2001 | |

* cited by examiner

*Primary Examiner* — Ali Z Fadhel

(57) ABSTRACT

This disclosure relates to catalysts comprising gallium, cerium, and a mixed oxide support useful in the dehydrogenation of hydrocarbons, to methods for making such catalysts, and to methods for dehydrogenating hydrocarbons with such catalysts. For example, in one embodiment, a catalyst composition includes gallium oxide, present in the composition in an amount within the range of about 0.1 wt. % to about 30 wt. %, cerium oxide, present in the composition in an amount within the range of about 0.1 wt. % to about 15 wt. %, a promoter, M1, selected from Pt, Ir, La, or a mixture thereof, present in the composition in an amount within the range of about 0.005 wt. % to about 4 wt. %, a promoter, M2, selected from the group 1 elements (e.g., Li, Na, K, Cs), present in the composition in an amount within the range of about 0.05 wt. % to about 3 wt. %, and a support, S1, selected from alumina, silica, zirconia, titania, or a mixture thereof, present in the composition in an amount within the range of about 60 wt. % to about 99 wt. %.

20 Claims, 6 Drawing Sheets

(51) Int. Cl.
*B01J 37/02* (2006.01)
*B01J 21/04* (2006.01)
*B01J 21/12* (2006.01)
*B01J 37/08* (2006.01)
*B01J 37/03* (2006.01)
*B01J 23/00* (2006.01)

DEHYDROGENATION CATALYSTS AND METHODS FOR PREPARING AND USING THEM

CROSS-REFERENCE TO RELATED APPLICATIONS

This application claims the benefit of priority of U.S. Provisional Patent Application No. 62/622,201, filed Jan. 26, 2018, which is hereby incorporated herein by reference in its entirety.

BACKGROUND OF THE DISCLOSURE

Field of the Disclosure

This disclosure relates generally to catalyst materials and methods for preparing and using them. More particularly, the present disclosure relates to gallium-based catalysts comprising multiple metal oxide components, to methods for making such catalysts, and to methods for dehydrogenating hydrocarbons using such catalysts.

Technical Background

Alkane dehydrogenation is a recognized process for production of a variety of useful hydrocarbon products, such as in the dehydrogenation of propane to make propene for use in the polymer industry, dehydrogenation of n-butane to produce n-butene or alkylate and butadiene useful in tire production, and the dehydrogenation of isobutane to make isobutylene suitable for conversion to methyl tert-butyl ether, isooctane, and alkylates to supplement and enrich gasolines. Current commercial catalysts useful for catalytic dehydrogenation of light alkanes include $CrOx/Al_2O_3$ and $Pt—Sn/Al_2O_3$ catalysts, which have been in use for decades.

$CrOx/Al_2O_3$ dehydrogenation catalysts typically contain a majority of their chromium in the Cr(III) oxidation state on alumina surface. However, there typically remains a small amount of Cr(VI), which is carcinogenic and thus presents health risks during catalyst handling and operation. $Pt—Sn/Al_2O_3$ catalysts are expensive. Moreover, to provide a spent $Pt—Sn/Al_2O_3$ catalyst with initial activity, treatment during operation with $Cl_2$ containing gas is required. Such gases can be deadly and thus present significant risks during operation. They also can cause significant environmental chlorine pollution.

Gallium-based dehydrogenation catalysts have been known for about two decades. They are generally not hazardous, and their application presents no significant environmental issue. However, these catalysts have limitations in activity and stability, especially for the commercially important dehydrogenation of propane, n-butane, and isobutane.

Accordingly, there remains a need for gallium-based dehydrogenation catalysts that provide improved activity and stability, especially in the dehydrogenation of propane and isobutane.

SUMMARY OF THE DISCLOSURE

One aspect of the disclosure is a calcined dehydrogenation catalyst composition comprising
  gallium oxide, present in the composition in an amount within the range of about 0.1 wt. % to about 30 wt. %, calculated as $Ga_2O_3$ on a calcined basis;
  cerium oxide, present in the composition in an amount within the range of about 0.1 wt. % to about 15 wt. %, calculated as $CeO_2$ on a calcined basis;
  a promoter M1 selected from platinum, iridium, lanthanum, or a mixture thereof, present in the composition in an amount within the range of about 0.005 wt. % to about 4 wt. %, calculated as oxide on a calcined basis;
  a promoter M2 selected from the group 1 elements, present in the composition in an amount within the range of about 0.05 wt. % to about 3 wt. %, calculated as oxide on a calcined basis; and
  a support S1 selected from alumina, silica, zirconia, titania, or a mixture thereof, present in the composition in an amount within the range of about 60 wt. % to about 99 wt. %, calculated as oxide on a calcined basis.

Another aspect of the disclosure is a method for dehydrogenating hydrocarbon, the method comprising contacting a hydrocarbon feed with the catalyst under conditions sufficient to form a dehydrogenated hydrocarbon.

Other aspects of the disclosure will be apparent to the person of ordinary skill in the art in view of the disclosure herein.

DETAILED DESCRIPTION

Figure 1:
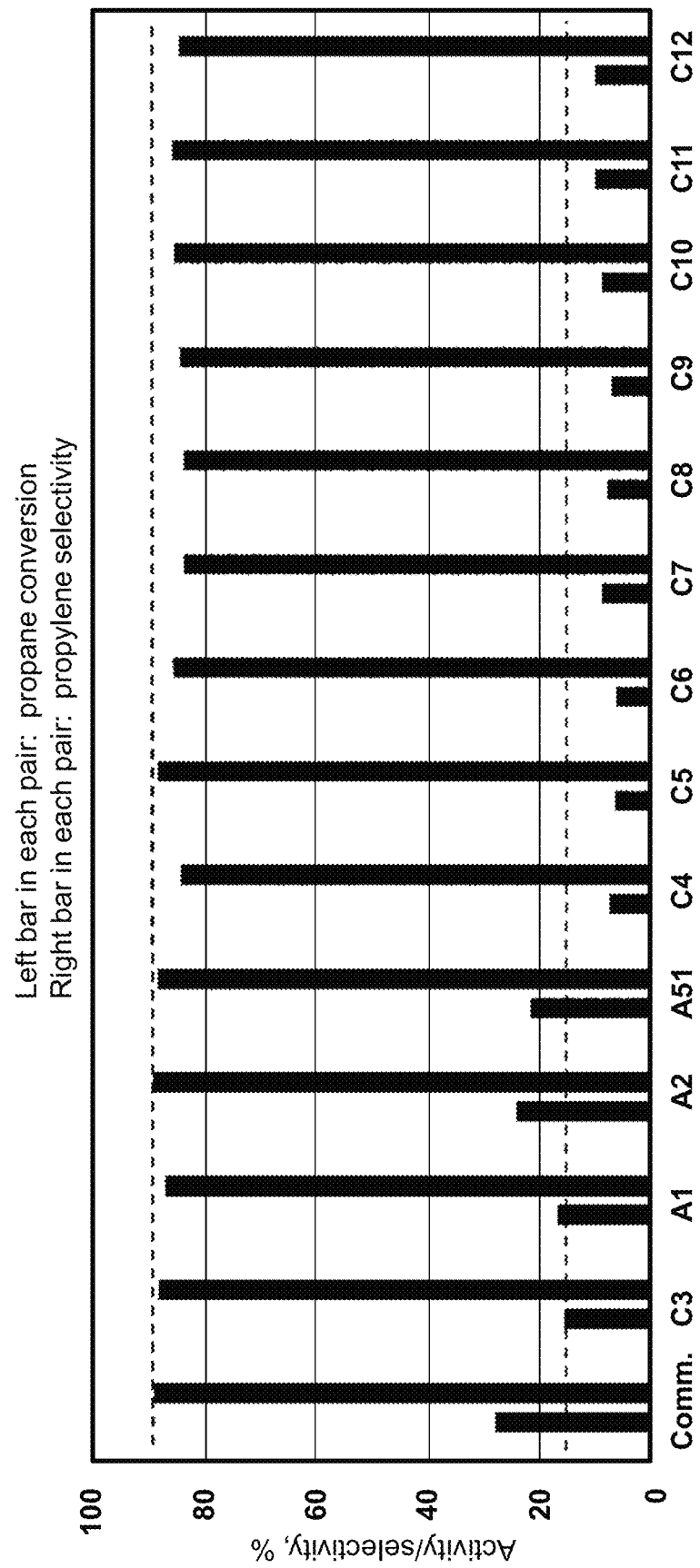
FIG. 1 is a bar graph showing (left-to-right in each set of bars) propane dehydrogenation conversion and propylene selectivity data for a variety of catalysts described herein.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Some embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The disclosure relates to dehydrogenation catalyst compositions that include gallium oxide, cerium oxide, one or more promoters selected from platinum, iridium, lanthanum, a mixture thereof, and the group 1 elements, and a mixed oxide support. The disclosure demonstrates that such catalysts, which may advantageously be free of chromium-containing materials, can exhibit performance comparable to or even better than conventional, commercially available catalysts.

One aspect of the disclosure is a calcined dehydrogenation catalyst composition. The catalyst composition includes gallium oxide, present in the composition in an amount within the range of about 0.1 wt. % to about 30 wt. %, calculated as $Ga_2O_3$ on a calcined basis, and cerium oxide, present in the composition in an amount within the range of about 0.1 wt. % to about 15 wt. %, calculated as $CeO_2$ on a calcined basis. The catalyst composition includes a promoter, M1, selected from Pt, Ir, La, and a mixture thereof, present in the composition in an amount within the range of about 0.005 wt. % to about 4 wt. %, and a promoter, M2, selected from group 1 elements (e.g., Li, Na, K, Cs), present in the composition in an amount within the range of about 0.05 wt. % to about 3 wt. %, each calculated as oxide on a calcined basis. And the catalyst composition includes a support, S1, selected from alumina, silica, zirconia, titania, and a mixture thereof, present in the composition in an amount within the range of about 60 wt. % to about 99 wt. %, calculated as oxide on a calcined basis.

In certain embodiments as otherwise described herein, a catalyst composition includes a promoter, M1-B, selected from Sn and Pd, present in the composition in an amount up to about 0.5 wt % (e.g., within the range of about 0.005 wt. % to about 0.5 wt. %), calculated as oxide on a calcined basis.

In certain embodiments as otherwise described herein, a catalyst composition includes a promoter, M3, selected from group 2 elements (e.g., Mg, Ca, Sr, Ba) and group 7-10 elements (e.g., Fe, Mn, Ni, Co), present in the composition in an amount up to about 10 wt. %, (e.g., within the range of about 0.05 wt. % to about 10 wt. %), calculated as oxide on a calcined basis.

As used herein, the term "oxide," including, e.g., "mixed oxide," "gallium oxide," "cerium oxide," etc., includes oxides in all forms and crystalline phases. For example, "gallium oxide" includes $Ga_2O_3$, $Ga_2O_x$ wherein x is within the range of 1 to 3, etc. Unless otherwise indicated, regardless of the actual stoichiometry of the oxide, oxides are calculated as the most stable oxide for purposes of weight percent determinations. For example, the person of ordinary skill in the art will appreciate that a non-stoichiometric oxide of gallium, or even another form of gallium, may still be calculated as $Ga_2O_3$. Moreover, unless otherwise indicated, the compositions are described on an as-calcined basis.

Without intending to be bound by theory, the present inventors believe that the gallium oxide acts as a primary catalytic species in dehydrogenation reactions mediated by the catalyst compositions described herein. As described above, in one aspect of the compositions of the disclosure, gallium oxide is present in an amount within the range of about 0.1 wt. % to about 30 wt. %, calculated as $Ga_2O_3$ on a calcined basis. For example, in certain embodiments of the compositions as otherwise described herein, gallium oxide is present in an amount within the range of about 0.1 wt. % to about 27.5 wt. %, or about 0.1 wt. % to about 25 wt. %, or about 0.1 wt. % to about 22.5 wt. %, or about 0.1 wt. % to about 20 wt. %, or about 0.1 wt. % to about 17.5 wt. %, or about 0.1 wt. % to about 15 wt. %, or about 0.1 wt. % to about 12.5 wt. %, or about 0.1 wt. % to about 10 wt. %, or about 0.5 wt. % to about 30 wt. %, or about 1 wt. % to about 30 wt. %, or about 2.5 wt. % to about 30 wt. %, or about 5 wt. % to about 30 wt. %, or about 7.5 wt. % to about 30 wt. %, or about 10 wt. % to about 30 wt. %, or about 12.5 wt. % to about 30 wt. %, or about 15 wt. % to about 30 wt. %, or about 17.5 wt. % to about 30 wt. %, or about 20 wt. % to about 30 wt. %, or about 0.5 wt. % to about 27.5 wt. %, or about 0.5 wt. % to about 25 wt. %, or about 1 wt. % to about 22.5 wt. %, or about 1 wt. % to about 20 wt. %, or about 1.5 wt. % to about 17.5 wt. %, or about 2 wt. % to about 15 wt. %, calculated as $Ga_2O_3$ on a calcined basis.

Without intending to be bound by theory, the present inventors believe that the cerium oxide acts as a primary catalytic species in dehydrogenation reactions mediated by the catalyst compositions described herein. As described above, in one aspect of the compositions of the disclosure, cerium oxide is present in an amount within the range of about 0.1 wt. % to about 15 wt. %, calculated as $CeO_2$ on a calcined basis. For example, in certain embodiments of the compositions as otherwise described herein, cerium oxide is present in an amount within the range of about 0.1 wt. % to about 14 wt. %, or about 0.1 wt. % to about 13 wt. %, or about 0.1 wt. % to about 12 wt. %, or about 0.1 wt. % to about 11 wt. %, or about 0.1 wt. % to about 10 wt. %, or about 0.1 wt. % to about 9 wt. %, or about 0.1 wt. % to about 8 wt. %, or about 0.1 wt. % to about 7 wt. %, or about 0.1 wt. % to about 6 wt. %, or about 0.1 wt. % to about 5 wt. %, or about 0.1 wt. % to about 4 wt. %, or about 0.1 wt. % to about 3 wt. %, or about 0.5 wt. % to about 15 wt. %, or about 1 wt. % to about 15 wt. %, or about 2 wt. % to about 15 wt. %, or about 3 wt. % to about 15 wt. %, or about 4 wt. % to about 15 wt. %, or about 5 wt. % to about 15 wt. %, or about 6 wt. % to about 15 wt. %, or about 7 wt. % to about 15 wt. %, or about 8 wt. % to about 15 wt. %, or about 9 wt. % to about 15 wt. %, calculated as $CeO_2$ on a calcined basis.

As described above, in one aspect of the compositions of the disclosure, M1, selected from platinum, iridium, lanthanum, or a mixture thereof, is present in an amount within the range of about 0.005 wt. % to about 4 wt. %, calculated as oxide on a calcined basis. For example, in certain embodiments of the compositions as otherwise described herein, M1 is selected from Pt and Ir. In another example, in certain embodiments of the compositions as otherwise described herein, M1 is selected from a mixture of Pt and La, and a mixture of Ir and La. In certain embodiments of the compositions as otherwise described herein, M1 is a mixture of Pt and La, present in a weight ratio of Pt to La within the range of about 5:1 to about 1:5, or about 4:1 to about 1:5, or about 3:1 to about 1:5, or about 2:1 to about 1:5, or about 1:1 to about 1:5, or about 5:1 to about 1:4, or about 5:1 to about 1:3, or about 5:1 to about 1:2, or about 5:1 to about 1:1, or about 4:1 to about 1:4, or about 3:1 to about 1:3, or about 2:1 to about 1:2. In certain embodiments of the compositions as otherwise described herein, M1 is a mixture of Ir and La, present in a weight ratio of Ir to La within the range of about 5:1 to about 1:5, or about 4:1 to about 1:5, or about 3:1 to about 1:5, or about 2:1 to about 1:5, or about 1:1 to about 1:5, or about 5:1 to about 1:4, or about 5:1 to about 1:3, or about 5:1 to about 1:2, or about 5:1 to about 1:1, or about 4:1 to about 1:4, or about 3:1 to about 1:3, or about 2:1 to about 1:2.

In certain embodiments of the compositions as otherwise described herein, M1 is present in the composition in an amount within the range of about 0.005 wt. % to about 3.75 wt. %, or about 0.005 wt. % to about 3.5 wt. %, or about 0.005 wt. % to about 3.25 wt. %, or about 0.005 wt. % to about 3 wt. %, or about 0.005 wt. % to about 2.75 wt. %, or about 0.005 wt. % to about 2.5 wt. %, or about 0.005 wt. % to about 2.25 wt. %, or about 0.005 wt. % to about 2 wt. %, or 0.005 wt. % to about 1.75 wt. %, or about 0.005 wt. % to about 1.5 wt. %, or about 0.005 wt. % to about 1.25 wt. %, or about 0.005 wt. % to about 1 wt. %, or about 0.005 wt.

% to about 0.9 wt. %, or about 0.005 wt. % to about 0.8 wt. %, or about 0.005 wt. % to about 0.7 wt. %, or about 0.005 wt. % to about 0.6 wt. %, or about 0.005 wt. % to about 0.5 wt. %, or about 0.01 wt. % to about 4 wt. %, or about 0.05 wt. % to about 4 wt. %, or about 0.1 wt. % to about 4 wt. %, or about 0.2 wt. % to about 4 wt. %, or about 0.3 wt. % to about 4 wt. %, or about 0.4 wt. % to about 4 wt. %, or about 0.5 wt. % to about 4 wt. %, or about 0.6 wt. % to about 4 wt. %, or about 0.7 wt. % to about 4 wt. %, or about 0.8 wt. % to about 4 wt. %, or about 0.9 wt. % to about 4 wt. %, or about 1 wt. % to about 4 wt. %, or about 0.0075 to about 3.5 wt. %, or about 0.0075 to about 3 wt. %, or about 0.01 wt. % to about 2.5 wt. %, or about 0.01 wt. % to about 2 wt. %, or about 0.01 wt. % to about 1.9 wt. %, or about 0.01 wt. % to about 1.8 wt. %, or about 0.01 wt. % to about 1.7 wt. %, or about 0.01 wt. % to about 1.6 wt. %, or about 0.01 wt. % to about 1.5 wt. %, or about 0.01 wt. % to about 1.4 wt. %, or about 0.01 wt. % to about 1.3 wt. %, or about 0.01 wt. % to about 1.2 wt. %, or about 0.015 wt. % to about 1.1 wt. %, or about 0.02 wt. % to about 1 wt. %, or about 0.02 wt. % to about 0.9 wt. %, or about 0.02 wt. % to about 0.8 wt. %, or about 0.02 wt. % to about 0.7 wt. %, or about 0.02 wt. % to about 0.6 wt. %, or about 0.02 wt. % to about 0.5 wt. %, calculated as oxide on a calcined basis.

As described above, in one aspect of the compositions of the disclosure, M2, selected from group 1 of the periodic table of the elements, is present in an amount within the range of about 0.05 wt. % to about 3 wt. %, calculated as oxide on a calcined basis. In certain embodiments of the compositions as otherwise described herein, M2 is selected from lithium, sodium, potassium, and cesium. For example, in certain embodiments of the compositions as otherwise described herein, M2 is potassium. In certain embodiments of the compositions as otherwise described herein, M2 is present in the composition in an amount within the range of about 0.05 wt. % to about 2.75 wt. %, or about 0.05 wt. % to about 2.5 wt. %, or about 0.05 wt. % to about 2.25 wt. %, or about 0.05 wt. % to about 2 wt. %, or about 0.05 wt. % to about 1.75 wt. %, or about 0.05 wt. % to about 1.5 wt. %, or about 0.05 wt. % to about 1.25 wt. %, or about 0.05 wt. % to about 1 wt. %, or about 0.1 wt. % to about 3 wt. %, or about 0.25 wt. % to about 3 wt. %, or about 0.5 wt. % to about 3 wt. %, or about 0.75 wt. % to about 3 wt. %, or about 1 wt. % to about 3 wt. %, or about 1.25 wt. % to about 3 wt. %, or about 1.5 wt. % to about 3 wt. %, or about 1.75 wt. % to about 3 wt. %, or about 2 wt. % to about 3 wt. %, or about 0.1 wt. % to about 2.5 wt. %, or about 0.1 wt. % to about 2 wt. %, or about 0.1 wt. % to about 1.75 wt. %, or about 0.1 wt. % to about 1.5 wt. %, or about 0.1 wt. % to about 1.25 wt. %, or about 0.1 wt. % to about 1 wt. %, calculated as oxide on a calcined basis.

In certain embodiments of the compositions as otherwise described herein, the composition further comprises a promoter, M1-B, selected from tin and palladium, present in an amount up to about 0.5 wt. %, e.g., within the range of about 0.005 wt. % to about 0.5 wt. %, calculated as oxide on a calcined basis. For example, in certain embodiments of the compositions as otherwise described herein, M1-B is tin. In certain embodiments of the compositions as otherwise described herein, M1-B is present in the composition in an amount within the range of about 0.005 wt. % to about 0.4 wt. %, or about 0.005 wt. % to about 0.3 wt. %, or about 0.005 wt. % to about 0.2 wt. %, or about 0.005 wt. % to about 0.1 wt. %, or about 0.005 wt. % to about 0.05 wt. %, or about 0.01 wt. % to about 0.5 wt. %, or about 0.025 wt. % to about 0.5 wt. %, or about 0.05 wt. % to about 0.5 wt. % or about 0.075 wt. % to about 0.5 wt. %, or about 0.1 wt. % to about 0.5 w.t % or about 0.2 wt. % to about 0.5 wt. %, or about 0.3 wt. % to about 0.5 wt. %, or about 0.0075 wt. % to about 0.4 wt. %, or about 0.01 wt. % to about 0.3 wt. %, or about 0.01 wt. % to about 0.2 wt. %, calculated as oxide on a calcined basis.

In certain embodiments of the compositions as otherwise described herein, the composition further comprises a promoter, M3, selected from group 2 and group 7-10 of the periodic table of the elements, present in an amount up to about 10 wt. %, e.g., within the range of about 0.05 wt. % to about 10 wt. %, calculated as oxide on a calcined basis. For example, in certain embodiments of the compositions as otherwise described herein, M3 is selected from magnesium, calcium, strontium, barium, manganese, iron, cobalt, and nickel. In another example, in certain embodiments of the compositions as otherwise described herein, M3 is selected from magnesium, calcium, strontium, barium, manganese, and iron. In certain embodiments of the compositions as otherwise described herein, M3 is present in the composition in an amount within the range of about 0.05 wt. % to about 9 wt. %, or about 0.05 wt. % to about 8 wt. %, or about 0.05 wt. % to about 7 wt. %, or about 0.05 wt. % to about 6 wt. %, or about 0.05 wt. % to about 5 wt. %, or about 0.1 wt. % to about 10 wt. %, or about 0.25 wt. % to about 10 wt. %, or about 0.5 wt. % to about 10 wt. %, or about 1 wt. % to about 10 wt. %, or about 2 wt. % to about 10 wt. %, or about 3 wt. % to about 10 wt. %, or about 4 wt. % to about 10 wt. %, or about 5 wt. % to about 10 wt. %, or about 0.075 wt. % to about 9 wt. %, or about 0.1 wt. % to about 8 wt. %, or about 0.1 wt. % to about 7 wt. %, or about 0.1 wt. % to about 6 wt. %, or about 0.1 wt. % to about 5 wt. %, calculated as oxide on a calcined basis.

For example, in certain embodiments of the compositions as otherwise described herein, gallium oxide is present in the composition in an amount within the range of about 1 wt. % to about 20 wt. %, about 1 wt. % to about 17.5 wt. %, or about 2 wt. % to about 15 wt. %, calculated as $Ga_2O_3$ on a calcined basis. In certain such embodiments, cerium oxide is present in the composition in an amount within the range of about 0.1 wt. % to about 10 wt. %, about 0.1 wt. % to about 5 wt. %, or about 0.1 wt. % to about 3 wt. %, calculated as $CeO_2$ on a calcined basis. In certain such embodiments, M1 is platinum, iridium, lanthanum, or a mixture thereof, present in the composition in an amount within the range of about 0.01 wt. % to about 2 wt. %, about 0.015 wt. % to about 1.5 wt. %, or about 0.02 wt. % to about 1 wt. %, calculated as oxide on a calcined basis. In certain such embodiments, M2 is potassium, present in the composition in an amount within the range of about 0.05 wt. % to about 2 wt. %, about 0.075 wt. % to about 1.5 wt. %, or about 0.1 wt. % to about 1 wt. %, calculated as $K_2O$ on a calcined basis. In certain such embodiments, M1-B is tin or palladium, present in an amount within the range of about 0.005 wt. % to about 0.5 wt. %, 0.0075 wt. % to about 0.3 wt. %, or about 0.01 wt. % to about 0.2 wt. %, calculated as $SnO_2$ or PdO, respectively, on a calcined basis. In certain such embodiments, M3 is selected from Mg, Ca, Sr, Ba, Mn, and Fe, present in an amount within the range of about 0.05 wt. % to about 7 wt. %, about 0.075 wt. % to about 6 wt. %, or about 0.1 wt. % to about 5 wt. %, calculated as oxide on a calcined basis As described above, in one aspect of the compositions of the disclosure, S1, selected from alumina, silica, zirconia, titania, or a mixture thereof, is present in an amount within the range of about 60 wt. % to about 99 wt. %, calculated as oxide on a calcined basis. For example, in certain embodiments of the compositions as otherwise described herein, S1 is alumina.

In certain embodiments of the compositions as otherwise described herein, S1 is a mixture of alumina and silica, present in a weight ratio within the range of about 0.5:1 to about 25:1. The person of ordinary skill in the art will appreciate that, as used herein, a "mixture" of alumina and silica includes homogeneous and heterogeneous mixtures. For example, the mixture of alumina and silica may comprise a covalently bound network including both silicon and aluminum atoms (e.g., —Si—O—Al—), or discrete domains of both silica and alumina. In certain embodiments of the compositions as otherwise described herein, S1 is a mixture of alumina and silica, present in a weight ratio within the range of about 0.5:1 to about 1:1, or about 1:1 to about 2:1, or about 2:1 to about 5:1, or about 5:1 to about 10:1, or about 10:1 to about 15:1, or about 15:1 to about 20:1, or about 20:1 to about 25:1.

In certain embodiments of the compositions as otherwise described herein, S1 is a mixture of alumina and zirconia, present in a weight ratio within the range of about 1:1 to about 25:1. For example, in certain embodiments of the compositions as otherwise described herein, S1 is a mixture of alumina and zirconia, present in a weight ratio within the range of about 1:1 to about 2:1, or about 2:1 to about 5:1, or about 5:1 to about 10:1, or about 10:1 to about 15:1, or about 15:1 to about 20:1, or about 20:1 to about 25:1.

In certain embodiments of the compositions as otherwise described herein, S1 is a mixture of alumina and titania, present in a weight ratio within the range of about 1.5:1 to about 25:1. For example, in certain embodiments of the compositions as otherwise described herein, S1 is a mixture of alumina and titania, present in a weight ratio within the range of about 1:5 to about 2:1, or about 2:1 to about 5:1, or about 5:1 to about 10:1, or about 10:1 to about 15:1, or about 15:1 to about 20:1, or about 20:1 to about 25:1.

In certain embodiments of the compositions as otherwise described herein, S1 is a mixture of alumina, silica, and zirconia, alumina and silica present in a weight ratio within the range of about 0.1:1 to about 25:1, and alumina and zirconia present in a weight ratio within the range of about 90:1 to about 40:1. For example, in certain embodiments of the compositions as otherwise described herein, S1 is a mixture of alumina, silica, and zirconia, alumina and silica present in a weight ratio within the range of about 0.1:1 to about 0.5:1, or about 0.5:1 to about 1:1, or about 1:1 to about 2:1, or about 2:1 to about 5:1, or about 5:1 to about 10:1, or about 10:1 to about 15:1, or about 15:1 to about 20:1, or about 20:1 to about 25:1, and alumina and zirconia present in a weight ratio within the range of about 90:1 to about 80:1, or about 80:1 to about 70:1, or about 70:1 to about 60:1, or about 60:1 to about 50:1, or about 50:1 to about 40:1.

The person of ordinary skill in the art will appreciate that the catalyst composition may, in some embodiments as otherwise described herein, be substantially free of chromium. For example, in certain embodiments of the compositions as otherwise described herein, the catalyst composition includes less than about 1 wt. %, or less than about 0.9 wt. %, or less than about 0.8 wt. %, or less than about 0.7 wt. %, or less than about 0.6 wt. %, or less than about 0.5 wt. %, or less than about 0.4 wt. %, or less than about 0.3 wt. %, or less than about 0.2 wt. %, or less than about 0.1 wt. %, or less than about 0.05 wt. %, or less than about 0.01 wt. % of chromium, calculated as $Cr_2O_3$.

The person of ordinary skill in the art will appreciate that the catalyst composition may, in some embodiments as otherwise described herein, be substantially free of each of the lanthanides other than lanthanum and cerium. For example, in certain embodiments of the compositions as otherwise described herein, the catalyst composition includes less than about 2 wt. %, or less than about 1.5 wt. %, or less than about 1 wt. %, or less than about 0.9 wt. %, or less than about 0.8 wt. %, or less than about 0.7 wt. %, or less than about 0.6 wt. %, or less than about 0.5 wt. %, or less than about 0.4 wt. %, or less than about 0.3 wt. %, or less than about 0.2 wt. %, or less than about 0.1 wt. %, or less than about 0.05 wt. %, or less than about 0.01 wt. % of the lanthanides other than lanthanum and cerium, calculated as $La_2O_3$ and $CeO_2$, respectively.

In certain desirable embodiments of the compositions as otherwise described herein, the total amount of the gallium oxide, cerium oxide, promoters (e.g., M1, M1-B, M2, and M3), and support (e.g., S1) is at least about 80 wt. %, or at least about 85 wt. %, or at least about 90 wt. %, or at least about 95 wt. %, or at least about 97.5 wt. %, or at least about 99 wt. % of the composition (i.e., calculated on an as-calcined oxide basis).

In certain desirable embodiments of the compositions as otherwise described herein, S1 comprises a covalent network structure, throughout which structure one or more of the gallium oxide, cerium oxide, and promoters (e.g., M1, M1-B, M2, and M3) are dispersed. For example, in certain embodiments of the compositions as otherwise described herein, S1 comprises the product of a hydrolysis-polycondensation reaction of one or more metal oxy compounds, e.g., performed in the presence of a gallium source, a cerium source, and one or more promoter sources. In certain such embodiments, the metal oxy compounds include metal alkoxides (e.g., aluminum isopropoxide, tetraethyl orthosilicate, titanium n-butoxide, and zirconium n-propoxide), metal oxynitrates (e.g., zirconyl nitrate), or metal hydroxides (e.g., aluminum hydroxide).

Another aspect of the disclosure is a method for preparing a dehydrogenation catalyst composition as described herein. The method includes providing a gallium source, a cerium source, an M1 source, an M2 source, and an S1 source, forming a solid from the solution (e.g., by a hydrolysis-polycondensation reaction), and calcining the solid so formed. The amounts and identities of the various components (e.g., promoters M1, M1-B, M2, M3 and support S1) can be as otherwise described above with respect to the catalyst compositions of the disclosure.

In certain embodiments of the methods as otherwise described herein, the gallium source is a gallium salt. For example, in certain embodiments of the methods as otherwise described herein, the gallium source is gallium nitrate or gallium acetylacetonate.

In certain embodiments of the methods as otherwise described herein, the cerium source is a cerium salt. For example, in certain embodiments of the methods as otherwise described herein, the cerium source is cerium nitrate.

In certain embodiments of the methods as otherwise described herein, the M1 source is a salt. For example, in certain embodiments of the methods as otherwise described herein, the M1 source is tetraamineplatinum(II) nitrate, hexachloroplatinate, iridium(IV) chloride, or lanthanum(III) nitrate.

In certain embodiments of the methods as otherwise described herein, the M2 source is a salt. For example, in certain embodiments of the methods as otherwise described herein, the M2 source is potassium nitrate.

In certain embodiments of the methods as otherwise described herein, the aqueous solution further comprises an M1-B source. In certain such embodiments, the M1-B source is a salt. For example, in certain embodiments of the methods as otherwise described herein, the M1-B source is tin(IV) chloride or palladium nitrate.

In certain embodiments of the methods as otherwise described herein, the aqueous solution further comprises an M3 source. In certain such embodiments, the M3 source is a salt. For example, in certain embodiments of the methods as otherwise described herein, the M3 source is magnesium nitrate, calcium nitrate, strontium nitrate, barium nitrate, manganese(II) nitrate, or iron(III) nitrate.

As described above, in one aspect of the methods of the disclosure, the method includes providing an aqueous solution comprising an S1 source. In certain embodiments of the methods as otherwise described herein, the S1 source includes one or more metal compounds selected from metal oxides and metal salts. For example, in certain embodiments of the methods as otherwise described herein, the S1 source includes one or more metal oxides selected from silica, alumina, or lanthania. In another example, in certain embodiments of the methods as otherwise described herein, the S1 source includes one or more metal salts selected from zirconium carbonate, aluminum nitrate, sodium silicate, or lanthanum nitrate.

In certain embodiments of the methods as otherwise described herein, the S1 source includes one or more metal oxy compounds selected from metal alkoxides, metal hydroxides, and metal oxynitrates. For example, in certain embodiments of the methods as otherwise described herein, the S1 source includes one or more of an aluminum alkoxide (e.g., aluminum isopropoxide), a silicon alkoxide (e.g., tetraethyl orthosilicate), a titanium alkoxide (e.g., titanium n-butoxide), and a zirconium alkoxide (e.g., zirconium n-propoxide). In another example, in certain embodiments of the methods as otherwise described herein, the S1 source includes an aluminum hydroxide (e.g., bayerite or boehmite). In another example, in certain embodiments of the methods as otherwise described herein, the S1 source includes a zirconium oxynitrate.

As described above, in one aspect of the methods of the disclosure, the method includes forming a solid from the solution, for example, by a hydrolysis-polycondensation reaction. This can be performed, for example, using conventional processes, including sol-gel processes familiar to the person of ordinary skill in the art. The solid can be, for example, in the form of a monolithic solvent, or in the form of particles, (e.g., as a slurry). In certain embodiments of the methods as otherwise described herein, forming the solid comprises performing a hydrolysis-polycondensation on at least a portion of the S1 source to provide a covalent network structure. For example, in certain embodiments of the methods as otherwise described herein, forming the solid comprises performing a hydrolysis-polycondensation on at least a portion of a metal oxy compound of the S1 source, e.g., aluminum alkoxide, silicon alkoxide, titanium alkoxide, zirconium alkoxide, aluminum hydroxide, zirconium hydroxide, zirconyl nitrate, etc. In certain embodiments of the methods as otherwise described herein, forming the solid is acid-catalyzed. In certain embodiments of the methods as otherwise described herein, forming the solid provides a covalent network structure, throughout which structure one or more of the gallium source, cerium source, M1 source, M1-B source, M2 source, and M3 source are dispersed.

In certain embodiments of the methods as otherwise described herein, the method includes heating the aqueous solution. For example, in certain embodiments of the methods as otherwise described herein, the aqueous solution is heated to a temperature within the range of about 60° C. to about 100° C., or about 70° C. to about 95° C., or about 80° C. to about 90° C. to form the solid.

In certain embodiments of the methods as otherwise described herein, the method includes aging the aqueous solution after acid is added. For example, in certain embodiments of the methods as otherwise described herein, the aqueous solution is aged to a time of period within the range of about 1 hour to about 3 hours, or about 1.5 hours to about 5 hours, or about 2 hours to about 7 hours to form the gel/slurry.

As described above, the method includes calcining the solid (e.g., after removing the solvent from the solid, for example, by filtration and drying). As the person of ordinary skill in the art will appreciate, further condensation reaction can occur during the calcining. In certain embodiments of the methods as otherwise described herein, the solid is calcined at a temperature within the range of about 300° C. to about 900° C. For example, in certain embodiments, the solid is calcined at a temperature within the range of about 350° C. to about 900° C., or about 400° C. to about 900° C., or about 450° C. to about 900° C., or about 500° C. to about 900° C., or about 550° C. to about 900° C., or about 300° C. to about 850° C., or about 300° C. to about 800° C., or about 300° C. to about 750° C., or about 300° C. to about 700° C., or about 300° C. to about 650° C., or about 350° C. to about 850° C., or about 400° C. to about 800° C., or about 450° C. to about 750° C.

In certain embodiments of the methods as otherwise described herein, the solid is calcined for a period of time within the range of about 5 min. to about 12 hr. For example, in certain embodiments of the methods as otherwise described herein, the solid is calcined for a period of time within the range of about 10 min. to about 12 hr., or about 15 min. to about 12 hr., or about 20 min. to about 12 hr., or about 30 min. to about 12 hr., or about 45 min. to about 12 hr., or about 1 hr. to about 12 hr., or about 1.5 hr. to about 12 hr., or about 2 hr. to about 12 hr., or about 5 min. to about 11 hr., or about 5 min. to about 10 hr., or about 5 min. to about 9 hr., or about 5 min. to about 8 hr., or about 5 min. to about 7.5 hr., or about 5 min. to about 7 hr., or about 5 min. to about 6.5 hr., or about 5 min. to about 6 hr., or about 5 min. to about 5.5 hr., or about 5 min. to about 5 hr., or about 30 min. to about 11 hr., or about 1 hr. to about 10 hr., or about 1.5 hr. to about 9 hr., or about 2 hr. to about 8 hr.

In certain embodiments of the methods as otherwise described herein, the solid is dried before calcination. In certain embodiments of the methods as otherwise described herein, the solid is dried at a temperature within the range of about 80° C. to about 240° C. For example, in certain embodiments of the methods as otherwise described herein, the solid is dried at a temperature within the range of about 80° C. to about 220° C., or about 80° C. to about 200° C., or about 80° C. to about 180° C., or about 100° C. to about 240° C., or about 120° C. to about 240° C., or about 140° C. to about 240° C., or about 100° C. to about 220° C., or about 120° C. to about 200° C., or about 140° C. to about 180° C.

In certain embodiments of the methods as otherwise described herein, the solid is dried for a period of time within the range of about 4 hr. to about 36 hr. For example, in certain embodiments of the methods as otherwise described herein, the solid is dried for a period of time within the range of about 4 hr. to about 30 hr., or about 4 hr. to about 24 hr., or about 4 hr. to about 22 hr., or about 4 hr. to about 20 hr., or about 6 hr. to about 36 hr., or about 8 hr. to about 36 hr., or about 10 hr. to about 36 hr., or about 12 hr. to about 36 hr., or about 6 hr. to about 30 hr., or about 8 hr. to about 24 hr., or about 10 hr. to about 22 hr., or about 12 hr. to about 20 hr.

Another aspect of the disclosure is a catalyst composition prepared by a method as described herein.

Advantageously, the present inventors have determined that use of catalyst compositions described herein can catalyze a hydrocarbon dehydrogenation reaction at an efficiency comparable to or better than conventional, commercially available catalyst materials.

The compositions described herein are especially useful in hydrocarbon dehydrogenation reactions. Accordingly, another aspect of the disclosure is a method for dehydrogenating alkanes that includes contacting a hydrocarbon feed with a catalyst composition as described herein under conditions sufficient to cause hydrocarbon dehydrogenation.

In some embodiments of the dehydrogenation methods as otherwise described herein, the hydrocarbon feed comprises one or more $C_3$-$C_5$ alkanes. For example, in certain embodiments of the dehydrogenation methods as otherwise described herein, the hydrocarbon feed comprises propane.

The contacting of the feed with the catalyst compositions described herein can be conducted in a variety of ways familiar to the person of ordinary skill in the art. Conventional equipment and processes can be used in conjunction with the catalyst compositions of the disclosure to provide beneficial performance. Thus, the catalyst may be contained in one bed within a reactor vessel or divided up among a plurality of beds within a reactor. The reaction system may contain one or more reaction vessels in series. The feed to the reaction zone can flow vertically upwards, or downwards through the catalyst bed in a typical plug flow reactor, or horizontally across the catalyst bed in a radial flow type reactor.

The contacting of the feed with the catalyst composition can be performed using conventional methods. For example, the feed may be introduced into the reaction zone containing the catalyst composition at a constant rate, or alternatively, at a variable rate.

In certain embodiments of the dehydrogenation methods as otherwise described herein, the feed is contacted with the provided catalyst composition at a liquid hourly space velocity (LHSV) within the range of about 0.5 $h^{-1}$ to about 4 $h^{-1}$. For example, in certain embodiments of the dehydrogenation methods as otherwise described herein, the feed is contacted with the provided catalyst composition at a liquid hourly space velocity of about 0.75 $h^{-1}$ to about 4 $h^{-1}$, or about 1 $h^{-1}$ to about 4 $h^{-1}$, or about 1.25 $h^{-1}$ to about 4 $h^{-1}$, or about 1.5 $h^{-1}$ to about 4 $h^{-1}$, or about 0.5 $h^{-1}$ to about 3.75 $h^{-1}$, or about 0.5 $h^{-1}$ to about 3.5 $h^{-1}$, or about 0.5 $h^{-1}$ to about 3.25 $h^{-1}$, or about 0.5 $h^{-1}$ to about 3 $h^{-1}$, or about 0.5 $h^{-1}$ to about 2.75 $h^{-1}$, or about 0.5 $h^{-1}$ to about 2.5 $h^{-1}$, or about 0.75 $h^{-1}$ to about 3.5 $h^{-1}$, or about 1 $h^{-1}$ to about 3 $h^{-1}$, or about 1.25 $h^{-1}$ to about 2.75 $h^{-1}$, or about 1.5 $h^{-1}$ to about 2.5 $h^{-1}$.

In certain embodiments of the dehydrogenation methods as otherwise described herein, the method is carried out at a temperature within the range of about 400° C. to about 750° C. For example, in certain embodiments of the dehydrogenation methods as otherwise described herein, the method is carried out at a temperature within the range of about 400° C. to about 700° C., or about 400° C. to about 650° C., or about 400° C. to about 600° C., or about 400° C. to about 550° C., or about 450° C. to about 750° C., or about 500° C. to about 750° C., or about 550° C. to about 750° C., or about 600° C. to about 750° C., or about 450° C. to about 700° C., or about 500° C. to about 650° C.

In certain embodiments of the dehydrogenation methods as otherwise described herein, the method is carried out at a pressure within the range of about 0.1 bar to about 1 bar. For example, in certain embodiments of the dehydrogenation methods as otherwise described herein, the methods is carried out at a pressure within the range of about 0.1 bar to about 0.9 bar, or about 0.1 bar to about 0.8 bar, or about 0.1 bar to about 0.7 bar, or about 0.1 bar to about 0.6 bar, or about 0.1 bar to about 0.5 bar, or about 0.2 bar to about 1 bar, or about 0.3 bar to about 1 bar, or about 0.4 bar to about 1 bar, or about 0.5 bar to about 1 bar, or about 0.2 bar to about 0.9 bar, or about 0.3 bar to about 0.8 bar, or about 0.4 bar to about 0.7 bar.

EXAMPLES

The Examples that follow are illustrative of specific embodiments of the invention, and various uses thereof. They are set forth for explanatory purposes only, and are not to be taken as limiting the invention.

Example 1. Catalyst Preparation

Catalyst A1 was prepared via sol-gel synthesis: 1.35 g Ga(NO$_3$)$_3$, 0.082 g KNO$_3$, 0.38 g Ce(NO$_3$)$_3$.6H$_2$O, and 0.044 g La(NO3)$_3$.6H2O were mixed together with 424.1 g DI water in a container at room temperature, then heated to 90° C. for 15 min. to reach a milk-like colloidal solution, to which 48.2 g aluminum isopropoxide was slowly added. The mixture was stirred at 90° C. for at least 30 min., then an aqueous solution containing 4.5 g HNO$_3$ and 1.4 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 4 hours.

Catalyst A2 was prepared via sol-gel synthesis: 1.32 g Ga(NO$_3$)$_3$, 0.09 g KNO$_3$, 0.38 g Ce(NO$_3$)$_3$.6H$_2$O, and 0.02 g Pt(NH$_3$)$_4$(NO$_3$)$_2$ were mixed together with 424.3 g DI water in a container at room temperature, then heated to 90° C. for 15 min. to reach a milk-like colloidal solution, to which 48.1 g aluminum isopropoxide was slowly added. The mixture was stirred at 90° C. for at least 30 min., then an aqueous solution containing 4.5 g HNO$_3$ and 1.4 g DI water was added to the mixture. The final mixture was further heated at 86-90° C. with vigorous stirring for 3 hours to provide a concentrated slurry/gel. The composition was dried in air at 120° C. for 16 hours and calcined at 600° C. in air for 4 hours.

Catalyst A3 was prepared via sol-gel synthesis: 5.4 g Ga(NO$_3$)$_3$, 0.32 g KNO$_3$, 1.53 g Ce(NO$_3$)$_3$.6H$_2$O, and 0.084 g Pt(NH$_3$)$_4$(NO$_3$)$_2$ were mixed together with 1696 g DI water in a closed container at room temperature, then heated to 90° C. for 15 min. to reach a milk-like colloidal solution, to which 192 g aluminum isopropoxide was slowly added. The mixture was stirred at 90° C. for at least 30 min., then an aqueous solution containing 18.0 g HNO$_3$ and 5.4 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A4 was prepared via sol-gel synthesis: 10.74 g Ga(NO$_3$)$_3$, 0.32 g KNO$_3$, 1.56 g Ce(NO$_3$)$_3$.6H$_2$O, 0.083 g Pt(NH$_3$)$_4$(NO$_3$)$_2$, and 0.085 g SnCl$_4$.4H$_2$O were mixed together with 1696 g DI water in a container at room temperature, then heated to 90° C. for 15 min. to reach a milk-like colloidal solution, to which 192 g aluminum isopropoxide was slowly added. The mixture was stirred at 90° C. for at least 30 min., then an aqueous solution containing 18.0 g $HNO_3$ and 5.4 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A5 was prepared via sol-gel synthesis: 5.40 g $Ga(NO_3)_3$, 0.34 g $KNO_3$, 1.53 g $Ce(NO_3)_3.6H_2O$, 0.083 g $IrCl_3$, and 0.088 g $SnCl_4.4H_2O$ were mixed together with 1696 g DI water in a closed container at room temperature, then heated to 90° C. for 15 min. to reach a homogenous solution, to which 192 g aluminum isopropoxide was slowly added. The mixture was stirred at 90° C. for at least 30 min., then an aqueous solution containing 18.0 g $HNO_3$ and 5.5 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A6 was prepared via sol-gel synthesis: 10.73 g $Ga(NO_3)_3$, 0.32 g $KNO_3$, 1.50 g $Ce(NO_3)_3.6H_2O$, 0.086 g $IrCl_3$, and 0.086 g $SnCl_4.4H_2O$ were mixed together with 1696 g DI water in a container at room temperature, then heated to ~90° C. for 15 min. to reach a homogenous solution, to which 192 g aluminum isopropoxide was slowly added. The mixture was stirred at 90° C. for at least 30 min., then an aqueous solution containing 18.0 g $HNO_3$ and 5.4 g DI water was added to the mixture. The final mixture was further heated at 86-90° C. with vigorous stirring for ~5 hours to provide a concentrated slurry/gel. The composition was dried in air at 120° C. for 16 hours and calcined at 600° C. in air for 4 hours.

Catalyst A7 was prepared via sol-gel synthesis: 10.76 g $Ga(NO_3)_3$, 0.32 g $KNO_3$, 1.52 g $Ce(NO_3)_3.6H_2O$, 0.081 g $IrCl_3$, and 0.087 g $SnCl_4.4H_2O$ were mixed together with 1696 g DI water in a closed container at room temperature, then heated to ~90° C. for 15 min. to reach a homogenous solution, to which 144.4 g aluminum isopropoxide and 48.0 g tetraethylorthosilicate were slowly added. The mixture was stirred at 90° C. for at least 30 min., then an aqueous solution containing 18.0 g $HNO_3$ and 5.4 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A8 was prepared via sol-gel synthesis: 21.5 g $Ga(NO_3)_3$, 0.33 g $KNO_3$, 1.53 g $Ce(NO_3)_3.6H_2O$, 0.081 g $IrCl_3$, and 0.088 g $SnCl_4.4H_2O$ were mixed together with 1696 g DI water in a container at room temperature, then heated to ~90° C. for 15 min. to reach a homogenous solution, to which 192 g aluminum isopropoxide was slowly added. The mixture was stirred at 90° C. for at least 30 min., then an aqueous solution containing 18.0 g $HNO_3$ and 5.4 g DI water was added to the mixture. The final mixture was further heated at 86-90° C. with vigorous stirring for ~7 hours to provide a concentrated slurry/gel. The composition was dried in air at 120° C. for 16 hours and calcined at 600° C. in air for 4 hours.

Catalyst A9 was prepared via sol-gel synthesis: 2.1 g $Ga(NO_3)_3$, 0.083 g $KNO_3$, 0.40 g $Ce(NO_3)_3.6H_2O$, 0.046 g $IrCl_3$, and 1.49 g $Mg(NO_3)_2.6H_2O$ were mixed together with 424 g DI water in a container at room temperature, then heated to ~90° C. for 15 min. to reach a homogenous solution, to which 48 g aluminum isopropoxide was slowly added. The mixture was stirred at 90° C. for at least 30 min., then an aqueous solution containing 4.5 g $HNO_3$ and 1.4 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 4 hours.

Catalyst A10 was prepared via sol-gel synthesis: 2.7 g $Ga(NO_3)_3$, 0.12 g $KNO_3$, 0.38 g $Ce(NO_3)_3.6H_2O$, 0.028 g $IrCl_3$, and 0.029 g $SnCl_4.4H_2O$ were mixed together with 424 g DI water in a container at room temperature, then heated to ~90° C. for 15 min. to reach a homogenous solution, to which 48 g aluminum isopropoxide was slowly added. The mixture was stirred at 90° C. for at least 30 min., then an aqueous solution containing 4.5 g $HNO_3$ and 1.4 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 2 hours.

Catalyst A11 was prepared via sol-gel synthesis: 10.73 g $Ga(NO_3)_3$, 0.32 g $KNO_3$, 1.52 g $Ce(NO_3)_3.6H_2O$, 0.082 g $IrCl_3$, 6.02 g $Mg(NO_3)_2.6H_2O$, and 0.081 g $SnCl_4.4H_2O$ were mixed together with 1696.1 g DI water in a container at room temperature, then heated to ~90° C. for 15 min. to reach a homogenous solution, to which 192.3 g aluminum isopropoxide was slowly added. The mixture was stirred at 90° C. for at least 30 min., then an aqueous solution containing 17.9 g $HNO_3$ and 5.4 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 2 hours.

Catalyst A12 was prepared via sol-gel synthesis: 8.28 g $Ga(NO_3)_3$, 0.33 g $KNO_3$, 1.56 g $Ce(NO_3)_3.6H_2O$, 0.155 g $IrCl_3$, and 6.05 g $Mg(NO_3)_2.6H_2O$ were mixed together with 1696.0 g DI water in a container at room temperature, then heated to ~90° C. for 15 min. to reach a homogenous solution, to which 192.1 g aluminum isopropoxide was slowly added. The mixture was stirred at 90° C. for at least 30 min., then an aqueous solution containing 18.0 g $HNO_3$ and 5.4 g DI water was added to the mixture. The final mixture was further heated at 86-90° C. with vigorous stirring for 6 hours to provide a concentrated slurry/gel. The composition was dried in air at 120° C. for 16 hours and calcined at 600° C. in air for 2 hours.

Catalyst A13 was prepared via sol-gel synthesis: 2.1 g $Ga(NO_3)_3$, 0.08 g $KNO_3$, 0.38 g $Ce(NO_3)_3.6H_2O$, 0.039 g $IrCl_3$, and 2.24 g $Mg(NO_3)_2.6H_2O$ were mixed together with 424.1 g DI water in a container at room temperature, then heated to ~90° C. for 15 min. to reach a homogenous solution, to which 48.0 g aluminum isopropoxide was slowly added. The mixture was stirred at 90° C. for at least 30 min., then an aqueous solution containing 4.5 g $HNO_3$ and 1.4 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 2 hours.

Catalyst A14 was prepared via sol-gel synthesis: 2.1 g $Ga(NO_3)_3$, 0.083 g $KNO_3$, 0.39 g $Ce(NO_3)_3.6H_2O$, 0.039 g $IrCl_3$, and 1.5 g $Ca(NO_3)_2$ were mixed together with 424.1 g DI water in a container at room temperature, then heated to ~90° C. for 15 min. to reach a homogenous solution, to which 48.2 g aluminum isopropoxide was slowly added. The mixture was stirred at 90° C. for at least 30 min., then an aqueous solution containing 4.5 g $HNO_3$ and 1.4 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 2 hours.

Catalyst A15 was prepared via sol-gel synthesis: 8.3 g $Ga(NO_3)_3$, 0.33 g $KNO_3$, 1.55 g $Ce(NO_3)_3.6H_2O$, 0.082 g $Pt(NH_3)_4(NO_3)_2$, and 1.55 g $Ca(NO_3)_2$ were mixed together with 1696.1 g DI water in a container at room temperature, then heated to ~90° C. for 15 min. to reach a milk-like solution, to which 192.2 g aluminum isopropoxide was slowly added. The mixture was stirred at 90° C. for at least 30 min., then an aqueous solution containing 17.9 g $HNO_3$ and 5.5 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A16 was prepared via sol-gel synthesis: 8.3 g $Ga(NO_3)_3$, 0.33 g $KNO_3$, 1.55 g $Ce(NO_3)_3.6H_2O$, 0.082 g $Pt(NH_3)_4(NO_3)_2$, and 1.83 g $Mg(NO_3)_2.6H_2O$ were mixed together with 1696.0 g DI water in a container at room temperature, then heated to ~90° C. for 15 min. to reach a milk-like colloidal solution, to which 144.6 g aluminum isopropoxide and 48.7 g tetraethyl orthosilicate were slowly added. The mixture was stirred at 90° C. for at least 30 min., then an aqueous solution containing 17.9 g $HNO_3$ and 5.5 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A17 was prepared via sol-gel synthesis: 5.36 g $Ga(NO_3)_3$, 0.085 g $KNO_3$, 0.39 g $Ce(NO_3)_3.6H_2O$, 0.023 g $SnCl_4.4H_2O$ 0.021 g $Pt(NH_3)_4(NO_3)_2$, and 1.53 g $Mg(NO_3)_2.6H_2O$ were mixed together with 423.9 g DI water in a container at room temperature, then heated to ~90° C. for 15 min. to reach a milk-like colloidal solution, to which 35.9 g aluminum isopropoxide and 12.0 g zirconyl nitrate were slowly added. The mixture was stirred at 90° C. for at least 30 min., then an aqueous solution containing 4.5 g $HNO_3$ and 1.5 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 4 hours.

Catalyst A18 was prepared via sol-gel synthesis: 8.5 g $Ga(NO_3)_3$, 0.52 g $KNO_3$, 1.72 g $Ce(NO_3)_3.6H_2O$, 1.82 g $Pt(NH_3)_4(NO_3)_2$, and 1.89 g $Mg(NO_3)_2.6H_2O$ were mixed together with 1696 g DI water in a container at room temperature, then heated to ~90° C. for 15 min. to reach a milk-like colloidal solution, to which 144.5 g aluminum isopropoxide and 48.7 g tetraethyl orthosilicate were slowly added. The mixture was stirred at ~90° C. for at least 30 min., then an aqueous solution containing 17.9 g $HNO_3$ and 5.5 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A19 was prepared via sol-gel synthesis: 8.4 g $Ga(NO_3)_3$, 0.50 g $KNO_3$, 1.59 g $Ce(NO_3)_3.6H_2O$, 1.83 g $Pt(NH_3)_4(NO_3)_2$, and 0.71 g $Mn(NO_3)_2.4H_2O$ were mixed together with 1696.7 g DI water in a container at room temperature, then heated to ~90° C. for 15 min. to reach a milk-like colloidal solution, to which 144.5 g aluminum isopropoxide and 50.8 g tetraethyl orthosilicate were slowly added. The mixture was stirred at 90° C. for at least 30 min., then an aqueous solution containing 17.98 g $HNO_3$ and 5.57 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A20 was prepared via sol-gel synthesis: 8.29 g $Ga(NO_3)_3$, 0.46 g $KNO_3$, 1.53 g $Ce(NO_3)_3.6H_2O$, 1.81 g $Pt(NH_3)_4(NO_3)_2$, and 5.98 g $Ca(NO_3)_2$ were mixed together with 1696.7 g DI water in a container at room temperature, then heated to ~90° C. for 15 min. to reach a milk-like colloidal solution, to which 144.5 g aluminum isopropoxide and 52.8 g tetraethyl orthosilicate were slowly added. The mixture was stirred at 90° C. for at least 30 min., then an aqueous solution containing 17.95 g $HNO_3$ and 5.42 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A21 was prepared via sol-gel synthesis: 21.76 g $Ga(NO_3)_3$, 0.45 g $KNO_3$, 1.52 g $Ce(NO_3)_3.6H_2O$, 1.82 g IrCl3, 0.1 g $SnCl_4.4H_2O$, and 1.82 g $Mg(NO_3)_2.6H_2O$ were mixed together with 1696.7 g DI water in a container at room temperature, then heated to ~90° C. for 15 min. to reach a homogenous solution, followed by slow addition of 182.9 g aluminum isopropoxide and 9.62 g tetraethyl orthosilicate. The mixture was stirred at 90° C. for at least 30 min., then an aqueous solution containing 18.0 g $HNO_3$ and 5.38 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A22 was prepared via sol-gel synthesis: 2.09 g $Ga(NO_3)_3$, 0.087 g $KNO_3$, 3.18 g $Ce(NO_3)_3.6H_2O$, 0.051 g IrCl3, 2.33 g ZrO(NO3), and 1.56 g $Mg(NO_3)_2.6H_2O$ were mixed together with 428.3 g DI water in a container at room temperature, then heated to ~90° C. for 15 min. to reach a homogenous solution, to which 38.8 g aluminum isopropoxide and 9.62 g tetraethyl orthosilicate were slowly added. The mixture was stirred at 90° C. for at least 30 min., then an aqueous solution containing 4.42 g $HNO_3$ and 1.4 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 4 hours.

Catalyst A23 was prepared via sol-gel synthesis: 2.07 g $Ga(NO_3)_3$, 0.12 g $KNO_3$, 0.39 g $Ce(NO_3)_3.6H_2O$, 0.027 g $Pt(NH_3)_4(NO3)_2$, and 1.51 g $Mg(NO_3)_2.6H_2O$ were mixed together with 424.4 g DI water in a container at room temperature, then heated to ~90° C. for 15 min. to reach a milk-like colloidal solution, to which 48.1 g aluminum isopropoxide and 2.60 g $ZrO(NO_3)_2$ were slowly added. The mixture was stirred at 90° C. for at least 30 min., then an aqueous solution containing 4.58 g $HNO_3$ and 1.4 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 4 hours.

Catalyst A24 was prepared via sol-gel synthesis: 8.34 g $Ga(NO_3)_3$, 0.33 g $KNO_3$, 1.57 g $Ce(NO_3)_3.6H_2O$, 0.082 g Pt(NH$_3$)$_4$(NO$_3$)$_2$, and 3.64 g Mg(NO$_3$)$_2$.6H$_2$O were mixed together with 1696.1 g DI water in a container at room temperature, then heated to ~90° C. for 15 min. to reach a milk-like colloidal solution, to which 144.5 g aluminum isopropoxide and 48.65 g tetraethyl orthosilicate were slowly added. The mixture was stirred at 90° C. for at least 30 min., then an aqueous solution containing 17.96 g HNO$_3$ and 5.50 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A25 was prepared via sol-gel synthesis: 2.07 g Ga(NO$_3$)$_3$, 0.12 g KNO$_3$, 0.39 g Ce(NO$_3$)$_3$.6H$_2$O, 0.024 g Pt(NH$_3$)$_4$(NO3)$_2$, and 1.50 g Mg(NO$_3$)$_2$.6H$_2$O were mixed together with 424.1 g DI water in a container at room temperature, then heated to ~90° C. for 15 min. to reach a milk-like colloidal solution, to which 48.0 g aluminum isopropoxide and 5.8 g titanium n-butoxide were slowly added. The mixture was stirred at 90° C. for at least 30 min., then an aqueous solution containing 4.64 g HNO$_3$ and 1.5 0 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 4 hours.

Catalyst A26 was prepared via sol-gel synthesis: 4.14 g Ga(NO$_3$)$_3$, 0.12 g KNO$_3$, 0.48 g Ce(NO$_3$)$_3$.6H$_2$O, 0.023 g Pt(NH$_3$)$_4$(NO3)$_2$, and 1.50 g Mg(NO$_3$)$_2$.6H$_2$O were mixed together with 424.1 g DI water in a container at room temperature, then heated to ~90° C. for 15 min. to reach a mil-like colloidal solution, to which 48.0 g aluminum isopropoxide and 2.6 g zirconyl nitrate were slowly added. The mixture was stirred at 90° C. for at least 30 min., then an aqueous solution containing 4.6 g HNO$_3$ and 1.5 g DI water was added to the mixture. The final mixture was further heated at 86-90° C. with vigorous stirring for ~3 hours to provide a concentrated slurry/gel. The composition was dried in air at 120° C. for 16 hours and calcined at 600° C. in air for 4 hours.

Catalyst A27 was prepared via sol-gel synthesis: 8.25 g Ga(NO$_3$)$_3$, 0.47 g KNO$_3$, 1.58 g Ce(NO$_3$)$_3$.6H$_2$O, 0.081 g Pt(NH$_3$)$_4$(NO3)$_2$, and 3.95 g Ca(NO$_3$)$_2$ were mixed together with 1697 g DI water in a container at room temperature, then heated to ~90° C. for 15 min. to reach a milk-like colloidal solution, to which 144.6 g aluminum isopropoxide and 53.6 g tetraethyl orthosilicate were slowly added. The mixture was stirred at 90° C. for at least 30 min., then an aqueous solution containing 17.97 g HNO$_3$ and 5.43 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A28 was prepared via sol-gel synthesis: 8.28 g Ga(NO$_3$)$_3$, 0.33 g KNO$_3$, 1.54 g Ce(NO$_3$)$_3$.6H$_2$O, 0.083 g Pt(NH$_3$)$_4$(NO3)$_2$, and 1.84 g Mg(NO$_3$)$_2$.6H$_2$O were mixed together with 1697 g DI water in a container at room temperature, then heated to ~90° C. for 15 min. to reach a milk-like colloidal solution, to which 144.7 g aluminum isopropoxide and 17.94 g tetraethyl orthosilicate were slowly added. The mixture was stirred at 90° C. for at least 30 min., then an aqueous solution containing 17.94 g HNO$_3$ and 5.44 g DI water was added to the mixture. The final mixture was further heated at 86-90° C. with vigorous stirring for ~6 hours to obtain concentrated slurry/gel. The composition was dried in air at 120° C. for 16 hours and calcined at 600° C. in air for 4 hours.

Catalyst A29 was prepared via sol-gel synthesis: 8.25 g Ga(NO$_3$)$_3$, 0.33 g KNO$_3$, 1.56 g Ce(NO$_3$)$_3$.6H$_2$O, 0.083 g Pt(NH$_3$)$_4$(NO3)$_2$, and 1.83 g Mg(NO$_3$)$_2$.6H$_2$O were mixed together with 1696 g DI water in a container at room temperature, then heated to ~90° C. for 15 min. to reach a milk-like colloidal solution, to which 125.3 g aluminum isopropoxide and 69.4 g tetraethyl orthosilicate were slowly added. The mixture was stirred at 90° C. for at least 30 min., then an aqueous solution containing 17.99 g HNO$_3$ and 5.47 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A30 was prepared via sol-gel synthesis: 8.26 g Ga(NO$_3$)$_3$, 0.33 g KNO$_3$, 1.55 g Ce(NO$_3$)$_3$.6H$_2$O, 0.082 g Pt(NH$_3$)$_4$(NO3)$_2$, and 1.82 g Mg(NO$_3$)$_2$.6H$_2$O were mixed together with 1697 g DI water in a container at room temperature, then heated to ~90° C. for 15 min. to reach a milk-like colloidal solution, to which 173.0 g aluminum isopropoxide and 9.57 g ZrO(NO$_3$)$_2$ were slowly added. The mixture was stirred at 90° C. for at least 30 min., then an aqueous solution containing 17.97 g HNO$_3$ and 5.52 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A31 was prepared via sol-gel synthesis: 8.25 g Ga(NO$_3$)$_3$, 0.33 g KNO$_3$, 1.55 g Ce(NO$_3$)$_3$.6H$_2$O, 0.082 g Pt(NH$_3$)$_4$(NO3)$_2$, and 1.84 g Mg(NO$_3$)$_2$.6H$_2$O were mixed together with 1696 g DI water in a container at room temperature, then heated to ~90° C. for 15 min. to reach a milk-like colloidal solution, to which 106.2 g aluminum isopropoxide and 87.0 g tetraethyl orthosilicate were slowly added. The mixture was stirred at 90° C. for at least 30 min., then an aqueous solution containing 17.95 g HNO$_3$ and 5.49 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A32 was prepared via sol-gel synthesis: 8.31 g Ga(NO$_3$)$_3$, 0.33 g KNO$_3$, 1.54 g Ce(NO$_3$)$_3$.6H$_2$O, 0.082 g Pt(NH$_3$)$_4$(NO3)$_2$, and 2.01 g Mg(NO$_3$)$_2$.6H$_2$O were mixed together with 1697 g DI water in a container at room temperature, then heated to ~90° C. for 15 min. to reach a milk-like colloidal solution, to which 153.8 g aluminum isopropoxide and 18.71 g ZrO(NO$_3$)$_2$ were slowly added. The mixture was stirred at 90° C. for at least 30 min., then an aqueous solution containing 17.95 g HNO$_3$ and 5.50 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A33 was prepared via sol-gel synthesis: 8.32 g Ga(NO$_3$)$_3$, 0.33 g KNO$_3$, 1.55 g Ce(NO$_3$)$_3$.6H$_2$O, 0.083 g Pt(NH$_3$)$_4$(NO3)$_2$, and 1.83 g Mg(NO$_3$)$_2$.6H$_2$O were mixed together with 1696 g DI water in a container at room temperature, then heated to ~90° C. for 15 min. to reach a milk-like colloidal solution, to which 134.6 g aluminum isopropoxide and 28.2 g ZrO(NO$_3$)$_2$ were slowly added. The mixture was stirred at 90° C. for at least 30 min., then an aqueous solution containing 17.94 g HNO$_3$ and 5.4 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A34 was prepared via sol-gel synthesis: 8.31 g $Ga(NO_3)_3$, 0.33 g $KNO_3$, 1.57 g $Ce(NO_3)_3.6H_2O$, 0.084 g $Pt(NH_3)_4(NO_3)_2$, and 1.83 g $Mg(NO_3)_2.6H_2O$ were mixed together with 1697 g DI water in a container at room temperature, then heated to ~90° C. for 15 min. to reach a milk-like colloidal solution, to which 172.8 g aluminum isopropoxide and 21.5 g titanium n-butoxide were slowly added. The mixture was stirred at 90° C. for at least 30 min., then an aqueous solution containing 17.92 g $HNO_3$ and 5.4 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A35 was prepared via sol-gel synthesis: 8.28 g $Ga(NO_3)_3$, 0.32 g $KNO_3$, 1.56 g $Ce(NO_3)_3.6H_2O$, 0.082 g $Pt(NH_3)_4(NO3)_2$, and 1.83 g $Mg(NO_3)_2.6H_2O$ were mixed together with 1697 g DI water in a container at room temperature, then heated to ~90° C. for 15 min. to reach a milk-like colloidal solution, to which 153.7 g aluminum isopropoxide and 43.3 g titanium n-butoxide were slowly added. The mixture was stirred at 90° C. for at least 30 min., then an aqueous solution containing 17.98 g $HNO_3$ and 5.5 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A36 was prepared via sol-gel synthesis: 8.28 g $Ga(NO_3)_3$, 0.33 g $KNO_3$, 1.58 g $Ce(NO_3)_3.6H_2O$, 0.084 g $Pt(NH_3)_4(NO3)_2$, and 1.83 g $Mg(NO_3)_2$ were mixed together with 1696 g DI water in a container at room temperature, then heated to ~90° C. for 15 min. to reach a milk-like colloidal solution, to which 144.6 g aluminum isopropoxide and 49.6 g tetraethyl orthosilicate were slowly added. The mixture was stirred at 90° C. for at least 30 min., then an aqueous solution containing 17.98 g $HNO_3$ and 5.4 g DI water was added to the mixture The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A37 was prepared via sol-gel synthesis: 8.27 g $Ga(NO_3)_3$, 0.46 g $KNO_3$, 1.56 g $Ce(NO_3)_3.6H_2O$, 0.023 g $Pt(NH_3)_4(NO3)_2$, and 4.03 g $Ca(NO_3)_2$ were mixed together with 1696 g DI water in a container at room temperature, then heated to ~90° C. for 15 min. to reach a milk-like colloidal solution, to which 144.6 g aluminum isopropoxide and 53.7 g tetraethyl orthosilicate were slowly added. The mixture was stirred at 90° C. for at least 30 min., then an aqueous solution containing 17.97 g $HNO_3$ and 5.5 g DI water was added to the mixture. The final mixture was further heated at 86-90° C. with vigorous stirring for ~6 hours to provide a concentrated slurry/gel. The composition was dried in air at 120° C. for 16 hours and calcined at 600° C. in air for 4 hours.

Catalyst A38 was prepared via sol-gel synthesis: 8.49 g $Ga(NO_3)_3$, 0.46 g $KNO_3$, 1.57 g $Ce(NO_3)_3.6H_2O$, 0.042 g $Pt(NH_3)_4(NO_3)_2$, and 0.79 g $Mn(NO_3)_2.6H_2O$ were mixed together with 1697 g DI water in a container at room temperature, then heated to ~90° C. for 15 min. to form a milk-like colloidal solution, to which 144.6 g aluminum isopropoxide and 50.7 g tetraethyl orthosilicate were slowly added. The mixture was stirred at 90° C. for 45 min., then an aqueous solution containing 18.0 g $HNO_3$ and 5.4 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A39 was prepared via sol-gel synthesis: 8.29 g $Ga(NO_3)_3$, 0.48 g $KNO_3$, 2.1 g $Ce(NO_3)_3.6H_2O$, 0.044 g $Pt(NH_3)_4(NO_3)_2$, and 4.36 g $Ca(NO_3)_2$ were mixed together with 1696 g DI water in a container at room temperature, then heated to ~90° C. for 15 min. to form a milk-like colloidal solution, to which 144.6 g aluminum isopropoxide, 53.6 g tetraethyl orthosilicate, and 1.0 g zirconyl nitrate were slowly added. The mixture was stirred at 90° C. for 60 min., then an aqueous solution containing 18.0 g $HNO_3$ and 5.5 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A40 was prepared via sol-gel synthesis: 8.3 g $Ga(NO_3)_3$, 0.46 g $KNO_3$, 1.6 g $Ce(NO_3)_3.6H_2O$, 0.044 g $Pt(NH_3)_4(NO3)_2$, and 4.1 g $Ca(NO_3)_2$ were mixed together with 1696 g DI water in a container at room temperature, then heated to ~90° C. for 15 min. to form a milk-like colloidal solution, to which 144.6 g aluminum isopropoxide, 53.8 g tetraethyl orthosilicate, and 0.7 g $La(NO3)3.6H2O$ were slowly added. The mixture was stirred at 90° C. for 50 min., then an aqueous solution containing 18.1 g $HNO_3$ and 5.5 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A41 was prepared via sol-gel synthesis: 8.3 g $Ga(NO_3)_3$, 0.48 g $KNO_3$, 1.6 g $Ce(NO_3)_3.6H_2O$, 0.043 g $Pt(NH_3)_4(NO3)_2$, and 1.22 g $Fe(NO_3)_3.9H_2O$ were mixed together with 1696 g DI water in a container at room temperature, then heated to ~90° C. for 15 min. to form a milk-like colloidal solution, to which 144.7 g aluminum isopropoxide and 50.6 g tetraethyl orthosilicate were slowly added. The mixture was stirred at 90° C. for 50 min., then an aqueous solution containing 18.1 g $HNO_3$ and 5.5 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A42 was prepared via sol-gel synthesis: 8.3 g $Ga(NO_3)_3$, 0.32 g $KNO_3$, 1.6 g $Ce(NO_3)_3.6H_2O$, 0.040 g $Pt(NH_3)_4(NO3)_2$, and 0.044 g $SnCl_4.4H_2O$, 3.6 g $Mg(NO_3)_2.6H_2O$ were mixed together with 1696 g DI water in a container at room temperature, then heated to ~90° C. for 15 min. to form a milk-like colloidal solution, to which 106.3 g aluminum isopropoxide and 86.9 g tetraethyl orthosilicate were slowly added. The mixture was stirred at 90° C. for 70 min., then an aqueous solution containing 17.9 g $HNO_3$ and 5.5 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A43 was prepared via sol-gel synthesis: 12.9 g $Ga(NO_3)_3$, 0.46 g $KNO_3$, 1.6 g $Ce(NO_3)_3.6H_2O$, 0.043 g $Pt(NH_3)_4(NO3)_2$, and 4.2 g $Ca(NO_3)_2$ were mixed together with 1696 g DI water in a container at room temperature, then heated to ~90° C. for 15 min. to form a milk-like colloidal solution, to which 124.7 g aluminum isopropoxide, 68.7 g tetraethyl orthosilicate, and 1.0 g zirconyl nitrate were slowly added. The mixture was stirred at 90° C. for 40 min., then an aqueous solution containing 18.0 g HNO$_3$ and 5.6 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A44 was prepared via sol-gel synthesis: 12.9 g Ga(NO$_3$)$_3$, 0.46 g KNO$_3$, 1.6 g Ce(NO$_3$)$_3$.6H$_2$O, 0.042 g Pt(NH$_3$)$_4$(NO3)$_2$, and 0.72 g Mg(NO$_3$)$_2$.4H$_2$O were mixed together with 1696 g DI water in a container at room temperature, then heated to ~90° C. for 15 min. to form a milk-like colloidal solution, to which 124.1 g aluminum isopropoxide, 68.7 g tetraethyl orthosilicate, and 1.0 g zirconyl nitrate were slowly added. The mixture was stirred at 90° C. for 60 min., then an aqueous solution containing 18.1 g HNO$_3$ and 5.5 g DI water was added to the mixture. The final mixture was further heated at 86-90° C. while vigorously stirring for ~6 hr to provide a concentrated slurry/gel. The as-made sample was dried in air at 120° C. for 16 hours and calcined at 600° C. in air for 4 hours.

Catalyst A45 was prepared via sol-gel synthesis: 8.3 g Ga(NO$_3$)$_3$, 0.46 g KNO$_3$, 1.6 g Ce(NO$_3$)$_3$.6H$_2$O, 0.041 g Pt(NH$_3$)$_4$(NO3)$_2$, and 1.94 g Ba(NO$_3$)$_2$ were mixed together with 1696 g DI water in a container at room temperature, then heated to ~90° C. for 15 min. to form a milk-like colloidal solution, to which 144.6 g aluminum isopropoxide, 55.6 g tetraethyl orthosilicate, and 0.4 g La(NO3)3.6H2O were slowly added. The mixture was stirred at 90° C. for ~60 min., then an aqueous solution containing 18.0 g HNO$_3$ and 5.5 g DI water was added to the mixture. The final mixture was further heated at 86-90° C. while vigorously stirring for ~6 hr to provide a concentrated slurry/gel. The as-made sample was dried in air at 120° C. for 16 hours and calcined at 600° C. in air for 4 hours.

Catalyst A46 was prepared via sol-gel synthesis: 8.5 g Ga(NO$_3$)$_3$, 0.44 g KNO$_3$, 1.6 g Ce(NO$_3$)$_3$.6H$_2$O, 0.043 g Pt(NH$_3$)$_4$(NO3)$_2$, and 4.0 g Ca(NO$_3$)$_2$ were mixed together with 1696 g DI water in a container at room temperature, then heated to ~90° C. for 15 min. to form a milk-like colloidal solution, to which 144.6 g aluminum isopropoxide, 55.6 g tetraethyl orthosilicate, and 0.4 g La(NO3)3.6H2O were slowly added. The mixture was stirred at 90° C. for ~50 min., then an aqueous solution containing 18.0 g HNO$_3$ and 5.5 g DI water was added to the mixture. The final mixture was further heated at 86-90° C. while vigorously stirring for ~6 hr to provide a concentrated slurry/gel. The as-made sample was dried in air at 120° C. for 16 hours and calcined at 600° C. in air for 4 hours.

Catalyst A47 was prepared via sol-gel synthesis: 8.3 g Ga(NO$_3$)$_3$, 0.47 g KNO$_3$, 1.6 g Ce(NO$_3$)$_3$.6H$_2$O, 0.041 g Pt(NH$_3$)$_4$(NO3)$_2$, and 2.5 g Sr(NO$_3$)$_2$ were mixed together with 1696 g DI water in a container at room temperature, then heated to ~90° C. for 15 min. to form a milk-like colloidal solution, to which 144.6 g aluminum isopropoxide, 55.7 g tetraethyl orthosilicate, and 0.4 g La(NO3)3.6H2O were slowly added. The mixture was stirred at 90° C. for ~50 min., then an aqueous solution containing 18.0 g HNO$_3$ and 5.5 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A48 was prepared via sol-gel synthesis: 8.3 g Ga(NO$_3$)$_3$, 0.46 g KNO$_3$, 1.6 g Ce(NO$_3$)$_3$.6H$_2$O, 0.023 g Pt(NH$_3$)$_4$(NO3)$_2$, and 4.0 g Ca(NO$_3$)$_2$ were mixed together with 1696 g DI water in a container at room temperature, then heated to ~90° C. for 15 min. to form a milk-like colloidal solution, to which 146.4 g aluminum isopropoxide and 38.5 g NALCO® 2327 were slowly added. The mixture was stirred at 90° C. for ~60 min., then an aqueous solution containing 18.1 g HNO$_3$ and 5.5 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A49 was prepared via sol-gel synthesis: 8.3 g Ga(NO$_3$)$_3$, 0.46 g KNO$_3$, 1.6 g Ce(NO$_3$)$_3$.6H$_2$O, 0.023 g Pt(NH$_3$)$_4$(NO3)$_2$, and 4.0 g Ca(NO$_3$)$_2$ were mixed together with 1696 g DI water in a container at room temperature, then heated to ~90° C. for 15 min. to form a milk-like colloidal solution, to which 55.6 g bayerite and 53.6 g tetraethyl orthosilicate were slowly added. The mixture was stirred at 90° C. for ~60 min., then an aqueous solution containing 18.0 g HNO$_3$ and 5.5 g DI water was added to the mixture. The final mixture was further heated at 86-90° C. while vigorously stirring for ~5 hr to provide a concentrated slurry/gel. The as-made sample was dried in air at 120° C. for 16 hours and calcined at 600° C. in air for 4 hours.

Catalyst A50 was prepared via sol-gel synthesis: 8.75 g Ga(NO$_3$)$_3$, 0.49 g KNO$_3$, 6.6 g Ce(NO$_3$)$_3$.6H$_2$O, 0.027 g Pt(NH$_3$)$_4$(NO3)$_2$, and 4.3 g Ca(NO$_3$)$_2$ were mixed together with 1696 g DI water in a container at room temperature, then heated to ~90° C. for 15 min. to form a milk-like colloidal solution, to which 144.6 aluminum isopropoxide and 53.6 g tetraethyl orthosilicate and 1.4 g zirconium n-propoxide were slowly added. The mixture was stirred at 90° C. for ~60 min., then an aqueous solution containing 18.0 g HNO$_3$ and 5.5 g DI water was added to the mixture. The final mixture was further heated at 86-90° C. while vigorously stirring for ~5.5 hr to provide a concentrated slurry/gel. The as-made sample was dried in air at 120° C. for 16 hours and calcined at 600° C. in air for 4 hours.

Comparative, alumina-supported gallium catalysts C1 and C2, lacking cerium and/or promoters, were prepared according to conventional methods.

Comparative catalyst C3 was prepared via sol-gel synthesis: 1.34 g Ga(NO$_3$)$_3$, 0.08 g KNO$_3$, and 0.38 g Ce(NO$_3$)$_3$.6H$_2$O were mixed together with 424 g DI water in a container at room temperature, then heated to 90° C. for at 15 min. to reach a homogenous solution, to which 48.1 g aluminum isopropoxide was slowly added. The mixture was stirred at 90° C. for at least 30 min., then an aqueous solution containing 4.5 g HNO$_3$ and 1.4 g DI water was added to the mixture. The final mixture was further heated at 86-90° C. with vigorous stirring for ~3 hours. The composition was dried in air at 120° C. for 16 hours and calcined at 600° C. in air for 4 hours.

TABLE 1

Catalyst Compositions

| Cat | Ga (wt. %) | Ce (wt. %) | M1 material | M1 wt. % | M1-B material | M1-B wt. % | M2 material | M2 wt. % |
|---|---|---|---|---|---|---|---|---|
| C1 | 3 | | | | | | K | 0.25 |
| C2 | 3 | | Pt | 0.1 | | | K | 0.25 |
| C3 | 3 | 1 | | | | | K | 0.25 |

TABLE 1-continued

Catalyst Compositions

| Cat | Ga (wt. %) | Ce (wt. %) | M1 material | M1 wt. % | M1-B material | M1-B wt. % | M2 material | M2 wt. % |
|---|---|---|---|---|---|---|---|---|
| A1 | 3 | 1 | La | 0.1 | | | K | 0.25 |
| A2 | 3 | 1 | Pt | 0.1 | | | K | 0.25 |
| A3 | 3 | 1 | Pt | 0.1 | Sn | 0.05 | K | 0.25 |
| A4 | 6 | 1 | Pt | 0.1 | Sn | 0.05 | K | 0.25 |
| A5 | 3 | 1 | Ir | 0.1 | Sn | 0.05 | K | 0.25 |
| A6 | 6 | 1 | Ir | 0.1 | Sn | 0.05 | K | 0.25 |
| A7 | 6 | 1 | Ir | 0.1 | Sn | 0.05 | K | 0.25 |
| A8 | 12 | 1 | Ir | 0.1 | Sn | 0.05 | K | 0.25 |
| A9 | 4.5 | 1 | Ir | 0.2 | | | K | 0.25 |
| A10 | 6 | 1 | Ir | 0.1 | Sn | 0.05 | K | 0.35 |
| A11 | 6 | 1 | Ir | 0.1 | Sn | 0.05 | K | 0.25 |
| A12 | 4.5 | 1 | Ir | 0.2 | | | K | 0.25 |
| A13 | 4.5 | 1 | Ir | 0.2 | | | K | 0.25 |
| A14 | 4.5 | 1 | Ir | 0.2 | | | K | 0.25 |
| A15 | 4.5 | 1 | Pt | 0.1 | | | K | 0.25 |
| A16 | 4.5 | 1 | Pt | 0.1 | | | K | 0.25 |
| A17 | 12 | 1 | Pt | 0.1 | Sn | 0.05 | K | 0.25 |
| A18 | 4.5 | 1 | Pt | 0.1 | | | K | 0.35 |
| A19 | 4.5 | 1 | Pt | 0.1 | | | K | 0.35 |
| A20 | 4.5 | 1 | Pt | 0.1 | | | K | 0.35 |
| A21 | 12 | 1 | Ir | 0.1 | Sn | 0.05 | K | 0.35 |
| A22 | 4.5 | 9.4 | Ir | 0.1 | | | K | 0.25 |
| A23 | 4.5 | 1 | Pt | 0.1 | | | K | 0.35 |
| A24 | 4.5 | 1 | Pt | 0.1 | | | K | 0.25 |
| A25 | 4.5 | 1 | Pt | 0.1 | | | K | 0.35 |
| A26 | 9 | 1 | Pt | 0.1 | | | K | 0.35 |
| A27 | 4.5 | 1 | Pt | 0.1 | | | K | 0.35 |
| A28 | 4.5 | 1 | Pt | 0.1 | | | K | 0.25 |
| A29 | 4.5 | 1 | Pt | 0.1 | | | K | 0.25 |
| A30 | 4.5 | 1 | Pt | 0.1 | | | K | 0.25 |
| A31 | 4.5 | 1 | Pt | 0.1 | | | K | 0.25 |
| A32 | 4.5 | 1 | Pt | 0.1 | | | K | 0.25 |
| A33 | 4.5 | 1 | Pt | 0.1 | | | K | 0.25 |
| A34 | 4.5 | 1 | Pt | 0.1 | | | K | 0.25 |
| A35 | 4.5 | 1 | Pt | 0.1 | | | K | 0.25 |
| A36 | 4.5 | 1 | Pt | 0.1 | | | K | 0.35 |
| A37 | 4.5 | 1 | Pt | 0.025 | | | K | 0.35 |
| A38 | 4.5 | 1 | Pt | 0.05 | | | K | 0.35 |
| A39 | 4.5 | 1 | Pt | 0.05 | | | K | 0.35 |
| A40 | 4.5 | 1 | Pt | 0.05 La 0.1 | | | K | 0.35 |
| A41 | 4.5 | 1 | Pt | 0.05 | | | K | 0.35 |
| A42 | 4.5 | 1 | Pt | 0.05 | | 0.05 | K | 0.25 |
| A43 | 7 | 1 | Pt | 0.05 | | | K | 0.35 |
| A44 | 7 | 1 | Pt | 0.05 | | | K | 0.35 |
| A45 | 4.5 | 1 | Pt | 0.05 La 0.1 | | | K | 0.35 |
| A46 | 4.5 | 1 | Pt | 0.05 La 0.1 | | | K | 0.35 |
| A47 | 4.5 | 1 | Pt | 0.05 La 0.1 | | | K | 0.35 |
| A48 | 4.5 | 1 | Pt | 0.025 | | | K | 0.35 |
| A49 | 4.5 | 1 | Pt | 0.025 | | | K | 0.35 |
| A50 | 4.5 | 4 | Pt | 0.025 | | | K | 0.35 |

TABLE 2

Catalyst Compositions

| Cat | M3 material | M3 wt. % | S1 Al$_2$O$_3$ (wt. %) | S1 SiO$_2$ (wt. %) | S1 ZrO$_2$ (wt. %) | S1 TiO$_2$ (wt. %) |
|---|---|---|---|---|---|---|
| C1 | | | | | | |
| C2 | | | | | | |
| C3 | | | 95.60 | | | |
| A1 | | | 95.6 | | | |
| A2 | | | 95.65 | | | |
| A3 | | | 95.65 | | | |
| A4 | | | 92.6 | | | |
| A5 | | | 95.6 | | | |
| A6 | | | 92.6 | | | |
| A7 | | | 69.45 | 23.15 | | |
| A8 | | | 86.6 | | | |
| A9 | Mg | 1 | 93.05 | | | |
| A10 | | | 92.5 | | | |
| A11 | Mg | 1 | 91.6 | | | |
| A12 | Mg | 1 | 93.05 | | | |
| A13 | Mg | 1.5 | 92.55 | | | |
| A14 | Ca | 2 | 91.05 | | | |
| A15 | Mg | 0.25 | 93.90 | | | |
| A16 | Mg | 0.3 | 70.39 | 23.46 | | |
| A17 | Mg | 1 | 64.2 | | 21.4 | |
| A18 | Mg | 0.3 | 70.31 | 23.44 | | |
| A19 | Mn | 0.3 | 70.31 | 23.44 | | |
| A20 | Ca | 3 | 68.29 | 22.76 | | |
| A21 | Mg | 0.3 | 81.89 | 4.31 | | |
| A22 | Mg | 1 | 84.75 | | 9.4 | |
| A23 | Mg | 1 | 83.75 | | 9.3 | |
| A24 | Mg | 0.6 | 70.16 | 23.39 | | |
| A25 | Mg | 1 | 83.75 | | | 9.31 |
| A26 | Mg | 1 | 79.7 | | 8.86 | |
| A27 | Ca | 2 | 69.04 | 23.01 | | |
| A28 | Mg | 0.3 | 79.77 | 14.08 | | |
| A29 | Mg | 0.3 | 61 | 32.85 | | |
| A30 | Mg | 0.3 | 84.47 | | 9.39 | |
| A31 | Mg | 0.3 | 51.62 | 42.23 | | |
| A32 | Mg | 0.3 | 75.08 | | 18.77 | |
| A33 | Mg | 0.3 | 65.7 | | 28.16 | |
| A34 | Mg | 0.3 | 84.47 | | | 9.39 |
| A35 | Mg | 0.3 | 75.08 | | | 18.77 |
| A36 | Mg | 0.3 | 70.36 | 23.46 | | |
| A37 | Ca | 2 | 69.08 | 23.03 | | |
| A38 | Mn | 0.3 | 70.35 | 23.45 | | |
| A39 | Ca | 2 | 68.33 | 22.78 | 0.9 | |
| A40 | Ca | 2 | 67.1 | 22.6 | | |
| A41 | Fe | 0.5 | 70.2 | 23.4 | | |
| A42 | Mg | 0.6 | 51.45 | 42.1 | | |
| A43 | Ca | 2 | 57.66 | 31.05 | 0.9 | |
| A44 | Mn | 0.3 | 58.75 | 31.64 | 0.9 | |
| A45 | Ba | 2 | 64.5 | 27.4 | | |
| A46 | Ca | 2 | 56.2 | 35.5 | | |
| A47 | Sr | 2 | 23.4 | 27.4 | | |
| A48 | Ca | 2 | 69.1 | 23 | | |
| A49 | Ca | 2 | 69.1 | 23 | | |
| A50 | Ca | 2 | 66.1 | 22.0 | 1.0 | |

Example 2. Propane Dehydrogenation

Catalyst compositions prepared according to Example 1 were tested as prepared in a fixed-bed reactor. A feed containing 100 mol. % propane was passed over a 15 ml catalyst bed at a total pressure of 0.5 bar, at 2.0 h$^{-1}$ liquid hourly space velocity (LHSV), at a temperature within the range of 540-600° C. The product effluent concentration at the reactor outlet was monitored with an in-line gas chromatograph (GC). Results are provided in Table 3, below.

TABLE 3

Propane Dehydrogenation

| Cat | T (° C.) | Propane Conversion (%) | Propylene Selectivity (%) |
|---|---|---|---|
| C1 | 540 | 11.0 | 87.8 |
| C2 | 540 | 8.7 | 91.9 |

TABLE 3-continued

Propane Dehydrogenation

| Cat | T (° C.) | Propane Conversion (%) | Propylene Selectivity (%) |
|---|---|---|---|
| C3 | 540 | 15.7 | 88.3 |
| A1 | 540 | 16.8 | 87.0 |
| A2 | 540 | 24.2 | 89.4 |
| A3 | 540 | 26.7 | 85.6 |
| A4 | 540 | 31.0 | 81.6 |
| A5 | 540 | 27.0 | 85.2 |
| A6 | 540 | 31.1 | 81.0 |
| A7 | 540 | 30.8 | 80.2 |
| A8 | 540 | 32.1 | 74.2 |
| A9 | 540 | 28.3 | 89.2 |
| A10 | 540 | 31.9 | 82.6 |
| A11 | 540 | 31.4 | 85.5 |
| A12 | 540 | 31.6 | 86.5 |
| A13 | 540 | 28.6 | 89.2 |
| A14 | 540 | 29.1 | 87.4 |
| A15 | 540 | 30.1 | 85.6 |
| A16 | 540 | 33.7 | 82.4 |
| A17 | 540 | 33.1 | 86.3 |
| A18 | 540 | 30.7 | 88.8 |
| A19 | 540 | 33.7 | 88.5 |
| A20 | 540 | 26.9 | 91.5 |
| A21 | 540 | 29.1 | 83.0 |
| A22 | 540 | 27.3 | 85.8 |
| A23 | 540 | 25.3 | 88.9 |
| A24 | 540 | 33.1 | 86.3 |
| A25 | 540 | 27.2 | 89.0 |
| A26 | 540 | 28.0 | 89.5 |
| A27 | 540 | 34.9 | 90.2 |
| A28 | 540 | 32.4 | 87.8 |
| A29 | 540 | 34.9 | 87.1 |
| A30 | 540 | 26.8 | 89.3 |
| A31 | 540 | 36.2 | 86.4 |
| A32 | 540 | 25.7 | 86.9 |
| A33 | 540 | 28.2 | 86.4 |
| A34 | 540 | 24.7 | 84.7 |
| A35 | 540 | 26.2 | 80.7 |
| A36 | 540 | 36.0 | 91.1 |
| A37 | 540 | 33.8 | 91.1 |
| A38 | 540 | 34.2 | 88.3 |
| A39 | 540 | 34.8 | 89.3 |
| A40 | 540 | 34.7 | 87.6 |
| A41 | 540 | 35.8 | 83.1 |
| A42 | 540 | 33.9 | 87.9 |
| A43 | 540 | 35.4 | 88.8 |
| A44 | 540 | 34.3 | 83.8 |
| A45 | 540 | 35.3 | 89.1 |
| A46 | 540 | 34.8 | 90.1 |
| A47 | 540 | 34.1 | 89.0 |
| A48 | 540 | 18.8 | 84.9 |
| A49 | 540 | 23.7 | 85.2 |
| A50 | 540 | 34.7 | 91.7 |

The results, shown in Table 3, demonstrate that the PtCe- and IrCe-promoted Ga catalysts provide hydrocarbon dehydrogenation efficiency better than conventional catalysts.

Example 3. Promoter Comparison

Catalysts C3 and A1-A2, catalysts prepared in a manner similar to that of Example 1 (catalyst A51 and comparative catalysts C4-C12, shown in Table 4, below), and a commercially available CrOx/Al$_2$O$_3$ catalyst (Comm.) were tested in a fixed-bed reactor in a manner similar to that of Example 2.

TABLE 4

Catalyst Compositions

| Cat | Ga (wt. %) | Ce (wt. %) | M1 material | M1 wt. % | M2 material | M2 wt. % | S1 Al$_2$O$_3$ (wt. %) |
|---|---|---|---|---|---|---|---|
| A51 | 3 | 1 | Ir | 0.1 | K | 0.25 | 95.65 |
| C4 | 3 | 1 | Ru | 0.1 | K | 0.25 | 95.65 |
| C5 | 3 | 1 | Pd | 0.1 | K | 0.25 | 95.65 |
| C6 | 3 | 1 | Co | 0.1 | K | 0.25 | 95.65 |
| C7 | 3 | 1 | Fe | 0.1 | K | 0.25 | 95.65 |
| C8 | 3 | 1 | Ni | 0.1 | K | 0.25 | 95.65 |
| C9 | 3 | 1 | In | 0.1 | K | 0.25 | 95.65 |
| C10 | 3 | 1 | Cu | 0.1 | K | 0.25 | 95.65 |
| C11 | 3 | 1 | Zn | 0.1 | K | 0.25 | 95.65 |
| C12 | 3 | 1 | Sn | 0.1 | K | 0.25 | 95.65 |

The results, shown in FIG. 1, demonstrate that the promoted Ga- and Ce-containing catalysts provide hydrocarbon dehydrogenation efficiency comparable to or better than conventional catalysts.

Example 4. 3-Cycle Activity/Selectivity Comparison

Catalysts A3-A7, a catalyst prepared in a manner similar to that of Example 1, and a commercially available CrOx/Al$_2$O$_3$ catalyst (Comm.) were tested in a fixed-bed reactor in a manner similar to that of Example 2, for three consecutive cycles. Activity and selectivity results for each cycle are provided in FIG. 2.

Figure 2:
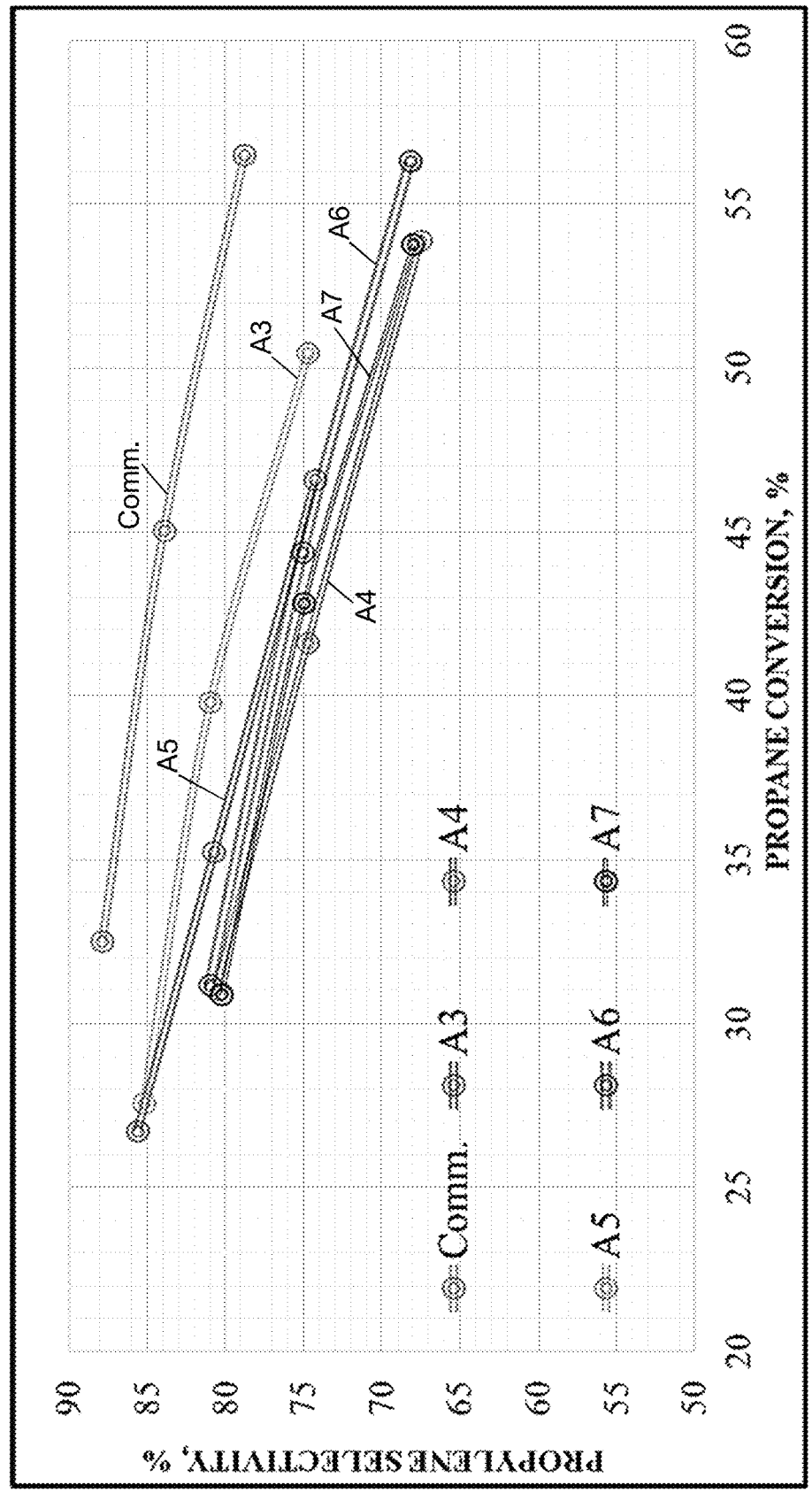
FIG. 2 is a line graph showing activity and selectivity data for a variety of catalysts described herein (top-to-bottom at the right side of the set of traces, comm., A3, A4, A5, A6 and A7, over three dehydrogenation cycles.

The results, shown in FIG. 2, demonstrate a negative correlation between conversion and selectivity. At a propane conversion of 45%, catalyst A5 showed the best selectivity of the compositions tested, which was about 6% lower than that of the commercially available CrOx/Al$_2$O$_3$ catalyst.

Figure 3:
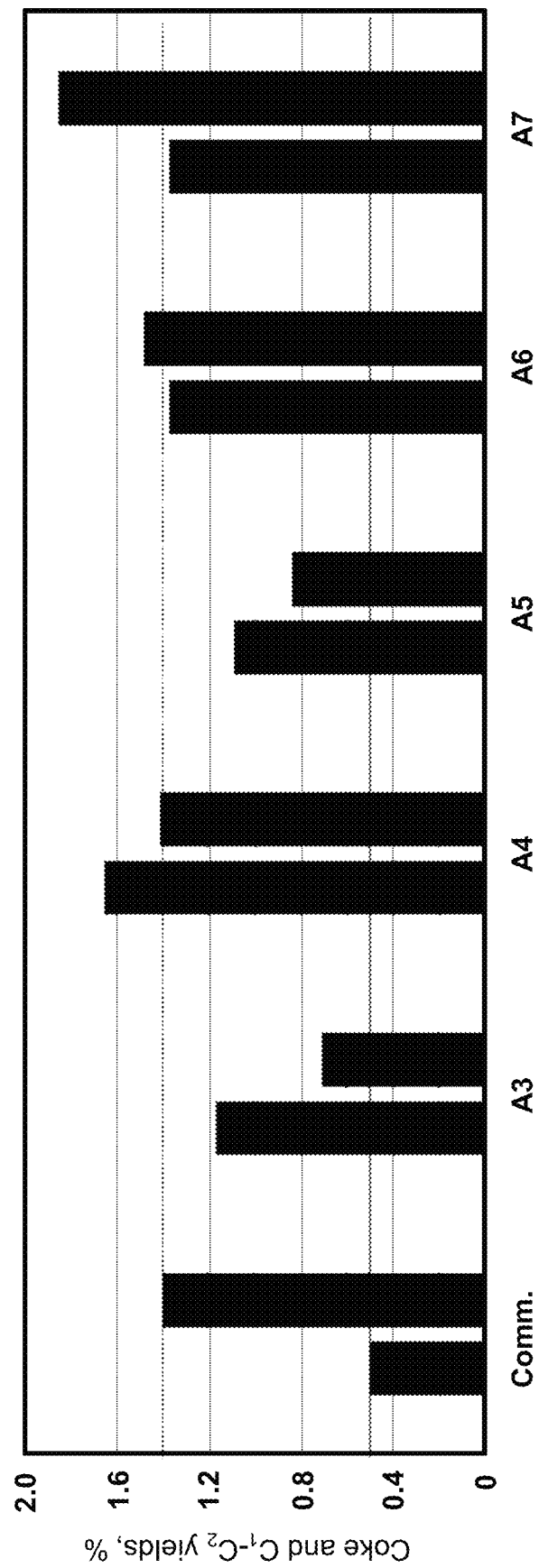
FIG. 3 is a bar graph showing (left-to-right in each set of bars) coke yield and $C_1$-$C_2$ byproduct yield data of a propane dehydrogenation cycle using a variety of catalysts described herein.

The coke and $C_1$-$C_2$ byproduct yields of the third cycle are provided in FIG. 3. The catalyst compositions showed a level of coke production at least twice that of the commercial catalyst. Without intending to be bound by theory, the present inventors believe that degree of coke formation is due to higher surface acidity, which acidity would also explain the difference in selectivity noted above. Catalyst A7 showed the highest $C_1$-$C_2$ byproduct yield. Without intending to be bound by theory, the present inventors believe that the byproduct yield increase relative to catalyst A6 can be attributed, in part, to the inclusion of silica.

Example 5. Performance Testing

To evaluate the effects of incorporation of silica into the catalyst compositions, catalysts A15, A28, A29, A31, and A36 were tested in a fixed-bed reactor in a manner similar to that of Example 2. Activity and selectivity results are provided in FIG. 4.

Figure 4:
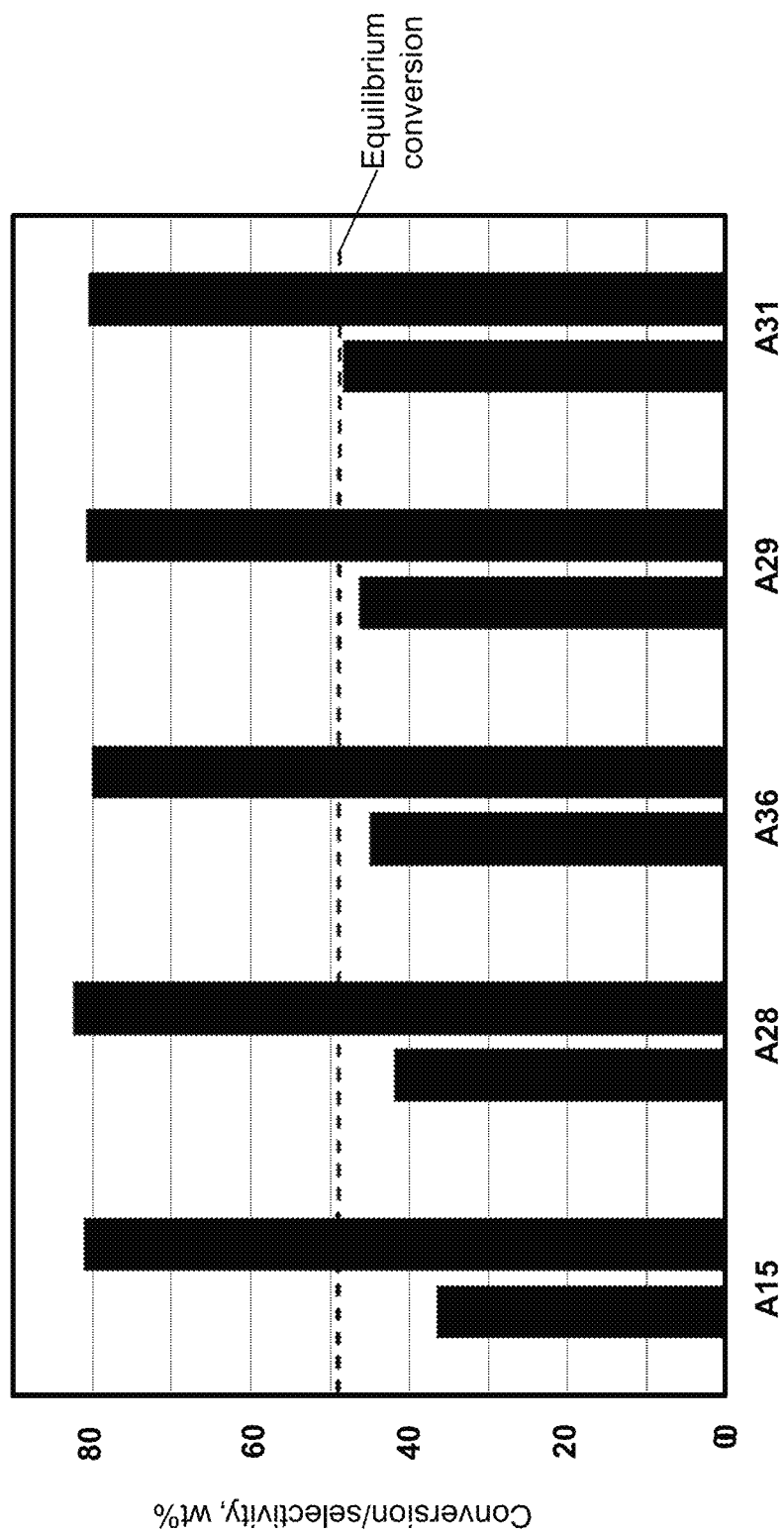
FIG. 4 is a bar graph showing (left-to-right in each set of bars) propane conversion and propylene selectivity data for a variety of catalysts described herein.

The results, provided in FIG. 4, show that propane conversion activity increased as the amount of silica included in the catalysts increased. The conversion activity of catalyst A31 was 48.2%, very close to the calculated thermodynamic equilibrium conversion (48.9%). Selectivity changed negligibly.

Example 6. Performance Testing

Figure 5:
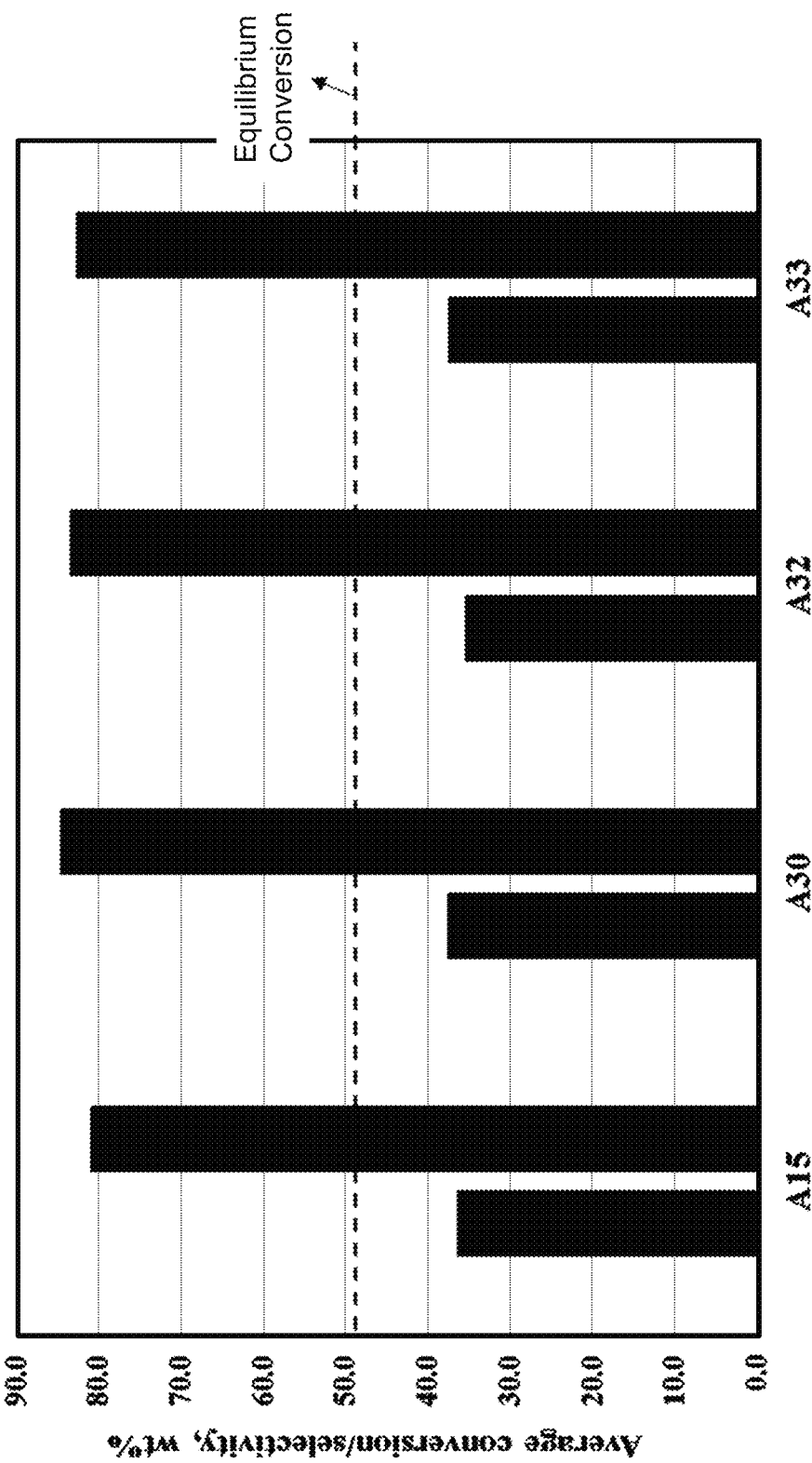
FIG. 5 is a bar graph showing (left-to-right in each set of bars) propane conversion and propylene selectivity data for a variety of catalysts described herein.

To evaluate the effects of incorporation of zirconia into the catalyst compositions, catalysts A15, A30, A32, and A33 were tested in a fixed-bed reactor in a manner similar to that of Example 2. Activity and selectivity results are provided in FIG. 5.

The results show that propane conversion activity and selectivity changed negligibly as the amount of zirconia included in the catalysts increased.

Example 7. Performance Testing

Figure 6:
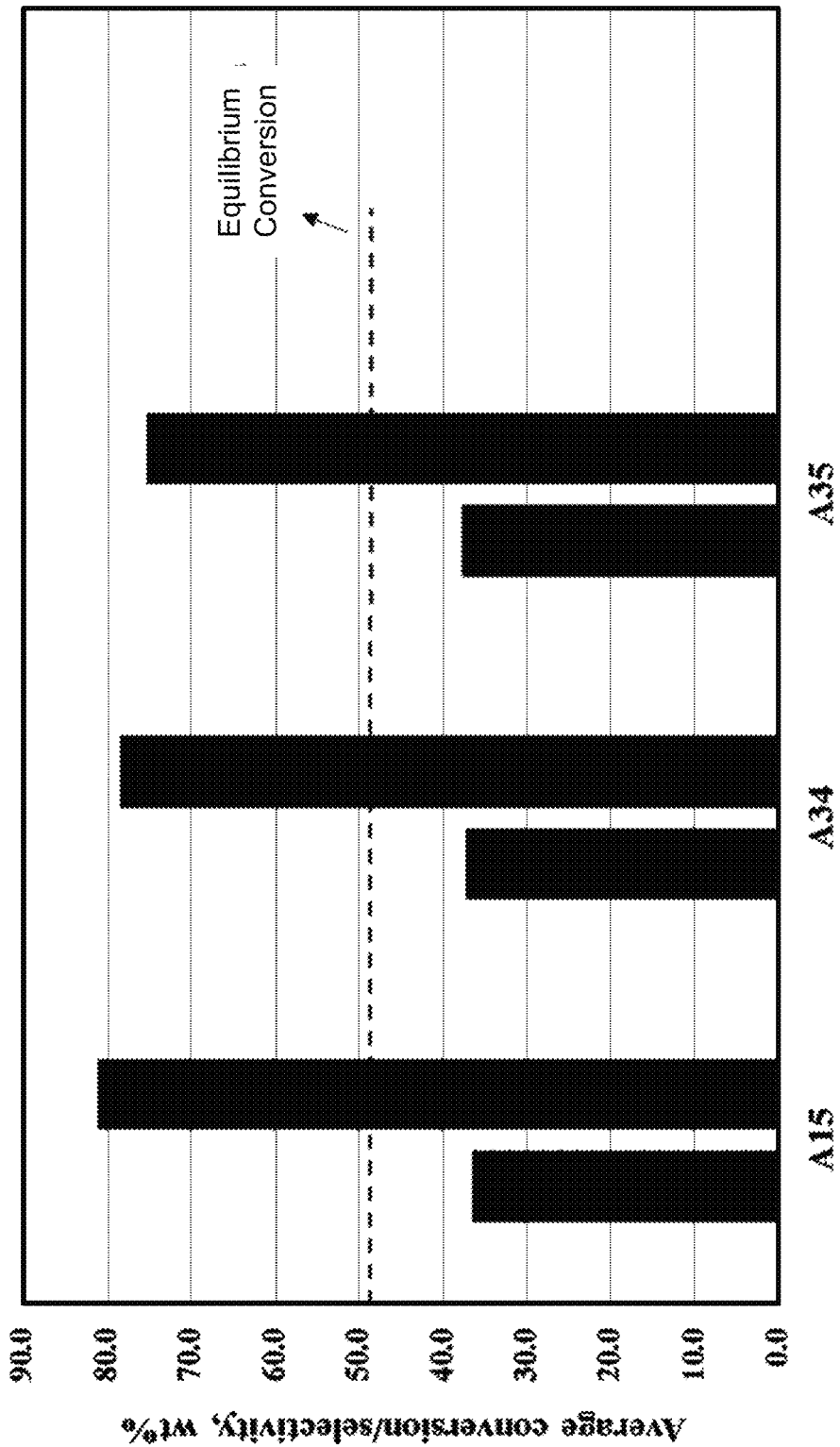
FIG. 6 is a bar graph showing (left-to-right in each set of bars) propane conversion and propylene selectivity data for a variety of catalysts described herein.

To evaluate the effects of incorporation of titania into the catalyst compositions, catalysts A15, A34, and A35 were tested in a fixed-bed reactor in a manner similar to that of Example 2. Activity and selectivity results are provided in FIG. 6.

The results show that propane conversion activity changed negligibly as the amount of titania included in the catalysts increased. Selectivity decreased gradually as the amount of titania included increased.

Example 8. Performance Testing

To evaluate the effects of incorporation of magnesium or calcium into the catalyst compositions, catalysts A24, A19, A27, and A29, and a commercially available $CrOx/Al_2O_3$ catalyst (Comm.) were tested in a fixed-bed reactor in a manner similar to that of Example 2. Activity and selectivity results are provided in Table 5, below.

TABLE 5

Propane Dehydrogenation

| Property | Comm. (wt. %) | A24 (wt. %) | A19 (wt. %) | A27 (wt. %) | A29 (wt. %) |
|---|---|---|---|---|---|
| 1000° F. | | | | | |
| C1 to C2 | 1.42 | 0.51 | 0.61 | 0.48 | 0.77 |
| Propane Conversion | 32.74 | 32.88 | 33.66 | 34.94 | 34.93 |
| Propylene Selectivity | 87.15 | 89.05 | 88.55 | 90.16 | 87.11 |
| Propylene Yield | 28.54 | 29.23 | 29.80 | 31.47 | 30.43 |
| Coke Yield | 0.60 | 0.93 | 1.07 | 0.85 | 1.15 |
| 1050° F. | | | | | |
| C1 to C2 | 3.06 | 1.29 | 1.63 | 1.46 | 2.17 |
| Propane Conversion | 45.78 | 43.51 | 43.58 | 46.58 | 46.33 |
| Propylene Selectivity | 83.66 | 86.02 | 83.26 | 86.89 | 81.91 |
| Propylene Yield | 38.33 | 37.48 | 36.28 | 40.47 | 37.97 |
| Coke Yield | 1.23 | 1.45 | 1.60 | 1.42 | 2.22 |
| 1100° F. | | | | | |
| C1 to C2 | 6.39 | 3.70 | 4.72 | 3.88 | 5.37 |
| Propane Conversion | 58.41 | 55.12 | 56.44 | 57.86 | 57.48 |
| Propylene Selectivity | 76.67 | 78.61 | 79.05 | 80.13 | 73.34 |
| Propylene Yield | 44.75 | 43.27 | 44.61 | 46.39 | 42.13 |
| Coke Yield | 3.20 | 3.27 | 3.60 | 2.97 | 4.56 |

The results show that the performance of the catalysts tested was acceptable.

Additional aspects of the disclosure are provided by the enumerated embodiments below, which can be combined and permuted in any fashion that is not logically or technically inconsistent.

Embodiment 1

A calcined dehydrogenation catalyst composition comprising
gallium oxide, present in the composition in an amount within the range of about 0.1 wt. % to about 30 wt. %, calculated as $Ga_2O_3$ on a calcined basis;
cerium oxide, present in the composition in an amount within the range of about 0.1 wt. % to about 15 wt. %, calculated as $CeO_2$ on a calcined basis;
a promoter M1 selected from platinum, iridium, lanthanum, or a mixture thereof, present in the composition in an amount within the range of about 0.005 wt. % to about 4 wt. %, calculated as oxide on a calcined basis;
a promoter M2 selected from the group 1 elements, present in the composition in an amount within the range of about 0.05 wt. % to about 3 wt. %, calculated as oxide on a calcined basis; and
a support S1 selected from alumina, silica, zirconia, titania, or a mixture thereof, present in the composition in an amount within the range of about 60 wt. % to about 99 wt. %, calculated as oxide on a calcined basis.

Embodiment 2

The catalyst composition of embodiment 1, wherein gallium oxide is present in the composition in an amount within the range of about 1 wt. % to about 20 wt. %, calculated as $Ga_2O_3$ on a calcined basis.

Embodiment 3

The catalyst composition of embodiment 1, wherein gallium oxide is present in the composition in an amount within the range of about 2 wt. % to about 15 wt. %, calculated as $Ga_2O_3$ on a calcined basis.

Embodiment 4

The catalyst composition of any of embodiments 1-3, wherein cerium oxide is present in the composition in an amount within the range of about 2 wt. % to about 15 wt. %, calculated as $CeO_2$ on a calcined basis.

Embodiment 5

The catalyst composition of any of embodiments 1-3, wherein cerium oxide is present in the composition in an amount within the range of about 0.1 wt. % to about 5 wt. %, calculated as $CeO_2$ on a calcined basis.

Embodiment 6

The catalyst composition of any of embodiments 1-5, wherein M1 is Pt or Ir or La or a combination of two or more thereof.

Embodiment 7

The catalyst composition of any of embodiments 1-5, wherein M1 is a mixture of Pt and La, present in a weight ratio of Pt to La of about 5:1 to about 1:5, e.g., about 2:1 to about 1:2.

Embodiment 8

The catalyst composition of any of embodiments 1-5, wherein M1 is a mixture of Ir and La, present in a weight ratio of Ir to La of about 5:1 to about 1:5, e.g., about 2:1 to about 1:2.

Embodiment 9

The catalyst composition of any of embodiments 1-8, wherein M1 is present in the composition in an amount within the range of about 0.01 wt. % to about 2 wt. %, calculated as oxide on a calcined basis.

Embodiment 10

The catalyst composition of any of embodiments 1-8, wherein M1 is present in the composition in an amount within the range of about 0.02 wt. % to about 1 wt. %, calculated as oxide on a calcined basis.

Embodiment 11

The catalyst composition of any of embodiments 1-10, wherein M2 is selected from Li, Na, K, and Cs.

Embodiment 12

The catalyst composition of any of embodiments 1-10, wherein M2 is K.

Embodiment 13

The catalyst composition of any of embodiments 1-12, wherein M2 is present in the composition in an amount within the range of about 0.05 wt. % to about 2 wt. %, calculated as oxide on a calcined basis.

Embodiment 14

The catalyst composition of any of embodiments 1-12, wherein M2 is present in the composition in an amount within the range of about 0.1 wt. % to about 1 wt. %, calculated as oxide on a calcined basis.

Embodiment 15

The catalyst composition of any of embodiments 1-14, further comprising a promoter M1-B selected from Sn and Pd, present in the composition in an amount up to about 0.5 wt. %, e.g., within the range of about 0.005 wt. % to about 0.5 wt. %, calculated as $SnO_2$ or PdO, respectively, on a calcined basis.

Embodiment 16

The catalyst composition of embodiment 15, wherein M1-B is Sn.

Embodiment 17

The catalyst composition of any of embodiments 15-16, wherein M1-B is present in the composition in an amount up to about 0.2 wt. %, e.g., within the range of about 0.01 wt. % to about 0.2 wt. %, calculated as oxide on a calcined basis.

Embodiment 18

The catalyst composition of any of embodiments 1-17, further comprising a promoter M3 selected from the group 2 and group 7-10 elements, present in the composition in an amount up to about 10 wt. %, e.g., within the range of about 0.05 wt. % to about 10 wt. %, calculated as oxide on a calcined basis.

Embodiment 19

The catalyst composition of embodiment 18, wherein M3 is selected from Mg, Ca, Sr, Ba, Mn, Fe, Co, and Ni.

Embodiment 20

The catalyst composition of embodiment 18, wherein M3 is selected from Mg, Ca, Sr, Ba, Mn, and Fe.

Embodiment 21

The catalyst composition of any of embodiments 18-20, wherein M3 is present in the composition in an amount within the range of about 0.05 wt. % to about 7 wt. %, calculated as oxide on a calcined basis.

Embodiment 22

The catalyst composition of any of embodiments 18-20, wherein M3 is present in the composition in an amount within the range of about 0.1 wt. % to about 5 wt. %, calculated as oxide on a calcined basis.

Embodiment 23

The catalyst composition of any of embodiments 1-22, wherein
- gallium oxide is present in the composition in an amount within the range of about 1 wt. % to about 20 wt. %, or about 2 wt. % to about 15 wt. %, calculated as $Ga_2O_3$ on a calcined basis;
- cerium oxide is present in the composition in an amount within the range of about 0.1 wt. % to about 10 wt. %, or about 0.1 wt. % to about 3 wt. %, calculated as $CeO_2$ on a calcined basis;
- M1 is Pt, Ir, La, or a mixture thereof, present in the composition in an amount within the range of about 0.01 wt. % to about 2 wt. %, or about 0.02 wt. % to about 1 wt. %, calculated as oxide on a calcined basis; and
- M2 is K, present in the composition in an amount within the range of about 0.05 wt. % to about 2 wt. %, or about 0.1 wt. % to about 1 wt. %, calculated as $K_2O$ on a calcined basis Embodiment 24

The catalyst composition of embodiment 23, further comprising M1-B, wherein M1-B is Sn or Pd, present in an amount within the range of about 0.005 wt. % to about 0.5 wt. %, or about 0.01 wt. % to about 0.2 wt. %, calculated as $SnO_2$ or PdO, respectively, on a calcined basis.

Embodiment 25

The catalyst composition of embodiment 23 or 24, further comprising M3, wherein M3 is selected from Mg, Ca, Sr, Ba, Mn, and Fe, present in an amount within the range of about 0.05 wt. % to about 7 wt. %, or about 0.1 wt. % to about 5 wt. %, calculated as oxide on a calcined basis.

Embodiment 26

The catalyst composition of any of embodiments 1-25, wherein S1 is alumina.

Embodiment 27

The catalyst composition of any of embodiments 1-25, wherein S1 is a mixture of alumina and silica, present in a weight ratio of alumina to silica within the range of about 0.5:1 to about 25:1.

Embodiment 28

The catalyst composition of any of embodiments 1-25, wherein S1 is a mixture of alumina and zirconia, present in a weight ratio of alumina to zirconia within the range of about 1:1 to about 25:1.

Embodiment 29

The catalyst composition of any of embodiments 1-25, wherein S1 is a mixture of alumina and titania, present in a weight ratio of alumina to titania within the range of about 1.5:1 to about 25:1.

Embodiment 30

The catalyst composition of any of embodiments 1-25, wherein
S1 is a mixture of alumina, silica, and zirconia;
alumina and silica are present in a weight ratio within the range of about 0.5:1 to about 25:1; and
alumina and zirconia are present in a weight ratio within the range of about 90:1 to about 40:1.

Embodiment 31

The catalyst composition of any of embodiments 1-30, wherein S1 is present in the composition in an amount within the range of about 70 wt. % to about 99 wt. %, or about 80 wt. % to about 99 wt. %, or about 90 wt. % to about 99 wt. %.

Embodiment 32

The catalyst composition of any of embodiments 1-30, wherein the composition comprises none of or less than 1 wt. % of the lanthanides other than lanthanum and cerium.

Embodiment 33

The catalyst composition of any of embodiments 1-30, wherein the total amount of gallium oxide, cerium oxide, M1, M1-B, M2, M3, and S1 is at least about 80 wt. %, at least about 85 wt. %, at least about 90 wt. %, at least about 95 wt. %, at least about 97.5 wt. %, or at least about 99 wt. % of the catalyst composition.

Embodiment 34

The catalyst composition of any of embodiments 1-33, wherein S1 comprises a covalent network structure.

Embodiment 35

The catalyst composition of embodiment 34, wherein S1 comprises the product of a hydrolysis-polycondensation of one or more metal oxy compounds, e.g., metal alkoxides, metal oxynitrates, or metal hydroxides.

Embodiment 36

The catalyst composition of any of embodiments 1-35, having no more than 1 wt % chromium, for example, no more than 0.5 wt % chromium or no more than 0.1 wt % chromium.

Embodiment 37

A method for preparing a dehydrogenation catalyst composition according to any of embodiments 1-36, comprising
providing an aqueous solution comprising
a gallium source;
a cerium source;
an M1 source;
an M2 source; and
an S1 source;
forming a solid from the solution; and
calcining the composition so formed.

Embodiment 38

A method according to embodiment 37, wherein the gallium source is a gallium salt, e.g., $Ga(NO_3)_3$ or gallium acetylacetonate Embodiment 39. A method according to embodiment 37 or 38, wherein the cerium source is a cerium salt, e.g., $Ce(NO_3)_3$.

Embodiment 40

A method according to any of embodiments 37-39, wherein the M1 source is a salt, e.g., $Pt(NH_3)_4(NO_3)_2$, $H_2PtCl_4$, $La(NO_3)_3$, or $IrCl_4$.

Embodiment 41

A method according to any of embodiments 37-40, wherein the M2 source is a salt, e.g., $KNO_3$.

Embodiment 42

A method according to any of embodiments 37-41, wherein the aqueous solution further comprises an M1-B source.

Embodiment 43

A method according to embodiment 42, wherein the M1-B source is a salt, e.g., $SnCl_4$ or $Pd(NO_3)_2$

Embodiment 44

A method according to any of embodiments 37-43, wherein the aqueous solution further comprises an M3 source.

Embodiment 45

A method according to embodiment 44, wherein the M3 source is a salt, e.g., $Mg(NO_3)_2$, $Ca(NO_3)_2$, $Sr(NO_3)_2$, $Ba(NO_3)_2$, $Mn(NO_3)_2$, or $Fe(NO_3)_3$.

Embodiment 46

A method according to any of embodiments 37-45, wherein the S1 source includes one or more metal compounds selected from metal oxides, e.g., silica alumina, and lanthania, and metal salts, e.g., zirconium carbonate, aluminum nitrate, or sodium silicate

Embodiment 47

A method according to any of embodiments 37-46, wherein the S1 source includes one or more metal oxy compounds selected from
- metal alkoxides, e.g., aluminum isopropoxide, tetraethyl orthosilicate, titanium n-butoxide, or zirconium n-propoxide;
- metal hydroxides, e.g., aluminum hydroxide; and
- metal oxynitrates, e.g., zirconyl nitrate.

Embodiment 48

A method according to embodiment 47, wherein forming the solid comprises polymerizing at least a portion of the S1 source to provide a covalent network structure.

Embodiment 49

A method according to embodiment 48, wherein forming the solid is acid-catalyzed.

Embodiment 50

A method according to embodiment 49, wherein one or more of the gallium source, cerium source, M1 source, M1-B source, M2 source, and M3 source are dispersed throughout the covalent network structure.

Embodiment 51

A method according to any of embodiments 37-50, wherein the aqueous solution is heated to a temperature within the range of about 60° C. to about 100° C., e.g., about 80° C. to about 90° C.

Embodiment 52

A method according to any of embodiments 37-50, wherein the aqueous solution is aged to a time of period within the range of about 1 hours to about 7 hours, e.g., about 1.5 hours to about 6 hours.

Embodiment 53

A method according to any of embodiments 37-52, wherein the calcination temperature is within the range of about 300° C. to about 900° C., e.g., about 450° C. to about 750° C.

Embodiment 54

A method according to any of embodiments 37-53, further comprising drying the solid before calcining.

Embodiment 55

A method according to embodiment 54, wherein the drying temperature is within the range of about 80° C. to about 240° C., e.g., about 120° C. to about 200° C.

Embodiment 56

A catalyst composition according to any of embodiments 1-36, made by a method of any of embodiments 37-55.

Embodiment 57

A method for dehydrogenating hydrocarbon, the method comprising contacting a hydrocarbon feed with the catalyst composition of any of embodiments 1-36 or 56.

Embodiment 58

A method according to embodiment 57, wherein the hydrocarbon feed comprises one or more $C_3$-$C_5$ alkanes.

Embodiment 59

A method according to embodiment 58, wherein the hydrocarbon feed comprises propane.

Embodiment 60

A method according to any of embodiments 57-59, wherein the hydrocarbon feed is contacted with the catalyst at a space velocity within the range of about 0.5 $h^{-1}$ to about 4 $h^{-1}$ LHSV.

Embodiment 61

A method according to any of embodiments 57-60, wherein the dehydrogenation is conducted at a temperature within the range of about 400° C. to about 750° C.

Embodiment 62

A method according to any of embodiments 57-61, wherein the dehydrogenation is conducted at a pressure within the range of about 0.1 bar to about 1 bar.

What is claimed is:

1. A calcined dehydrogenation catalyst composition comprising
   - gallium oxide, present in the composition in an amount within the range of about 1 wt. % to about 20 wt. %, calculated as $Ga_2O_3$ on a calcined basis;
   - cerium oxide, present in the composition in an amount within the range of about 0.1 wt. % to about 10 wt. %, calculated as $CeO_2$ on a calcined basis;
   - a promoter M1 selected from platinum, iridium, lanthanum, or a mixture thereof, present in the composition in an amount within the range of about 0.01 wt. % to about 2 wt. %, calculated as oxide on a calcined basis;
   - a promoter M2 selected from the group 1 elements, present in the composition in an amount within the range of about 0.05 wt. % to about 3 wt. %, calculated as oxide on a calcined basis; and
   - a support S1 selected from alumina, silica, zirconia, titania, or a mixture thereof, present in the composition in an amount within the range of about 60 wt. % to about 99 wt. %, calculated as oxide on a calcined basis.

2. The catalyst composition of claim 1, wherein M1 includes Ir.

3. The catalyst composition of claim 1, wherein M1 is present in the composition in an amount within the range of about 0.01 wt. % to about 1 wt. %, calculated as oxide on a calcined basis.

4. The catalyst composition of claim 1, wherein M2 is selected from Li, Na, K, and Cs.

5. The catalyst composition of claim 1, wherein M2 is present in the composition in an amount within the range of about 0.05 wt. % to about 2 wt. %, calculated as oxide on a calcined basis.

6. The catalyst composition of claim 1, further comprising a promoter M1-B selected from Sn and Pd, present in the composition in an amount within the range of about 0.005 wt. % to about 0.5 wt. %, calculated as $SnO_2$ or PdO, respectively, on a calcined basis.

7. The catalyst composition of claim 1, further comprising a promoter M3 selected from Mg, Ca, Sr, Ba, Fe, Co, and Ni, present in the composition in an amount within the range of about 0.05 wt. % to about 10 wt. %, calculated as oxide on a calcined basis.

8. The catalyst composition of claim 7, wherein M3 is selected from Mg and Ca, and is present in the composition in an amount within the range of about 0.05 wt. % to about 7 wt. %.

9. The catalyst composition of claim 1, wherein
gallium oxide is present in the composition in an amount within the range of about 2 wt. % to about 15 wt. %, calculated as $Ga_2O_3$ on a calcined basis;
cerium oxide is present in the composition in an amount within the range of about 0.1 wt. % to about 3 wt. %, calculated as $CeO_2$ on a calcined basis;
M1 is present in the composition in an amount within the range of about 0.01 wt. % to about 1 wt. %, calculated as oxide on a calcined basis; and
M2 is K, present in the composition in an amount within the range of about 0.05 wt. % to about 1 wt. %, calculated as $K_2O$ on a calcined basis.

10. The catalyst composition of claim 9, further comprising M3, wherein M3 is selected from Mg, Ca, Sr, Ba, and Fe, present in an amount within the range of about 0.05 wt. % to about 7 wt. %, calculated as oxide on a calcined basis.

11. The catalyst composition of claim 9, wherein M1 includes Ir.

12. The catalyst composition of claim 1, wherein S1 is a mixture of alumina and silica, a mixture of alumina and zirconia, or a mixture of alumina and titania.

13. The catalyst composition of claim 1, wherein
S1 is a mixture of alumina, silica, and zirconia;
alumina and silica are present in a weight ratio within the range of about 0.5:1 to about 25:1; and
alumina and zirconia are present in a weight ratio within the range of about 90:1 to about 40:1.

14. The catalyst composition of claim 1, wherein S1 is present in the composition in an amount within the range of about 70 wt. % to about 99 wt. %.

15. The catalyst composition of claim 1, wherein the composition comprises
none of or less than 1 wt. % of the lanthanides other than lanthanum and cerium; and
none of or less than 0.5 wt. % of chromium.

16. The catalyst composition of claim 1, optionally including a promoter M1-B selected from Sn and Pd, and optionally including a promoter M3 selected from Mg, Ca, Sr, Ba, and Fe, wherein the total amount of gallium oxide, cerium oxide, M1, M1-B, M2, M3, and S1 is at least about 97.5 wt. % of the catalyst composition.

17. A method for preparing a dehydrogenation catalyst composition according to claim 1, comprising
providing an aqueous solution comprising
a gallium source;
a cerium source;
an M1 source;
an M2 source; and
an S1 source;
forming a solid from the solution; and
calcining the solid so formed.

18. A method for dehydrogenating hydrocarbon, the method comprising contacting a hydrocarbon feed with the catalyst composition of claim 1.

19. The catalyst composition of claim 1, wherein S1 is a mixture of alumina and silica, present in a weight ratio of alumina to silica within the range of about 0.5:1 to about 25:1.

20. The catalyst composition of claim 1, wherein S1 is a mixture of alumina and zirconia, present in a weight ratio of alumina to zirconia within the range of about 1:1 to about 25:1.

* * * * *